US012749574B2

(12) United States Patent
Phillips et al.

(10) Patent No.: US 12,749,574 B2
(45) Date of Patent: Sep. 29, 2026

(54) SMART CORDS IN MEDICAL APPLICATIONS

(71) Applicant: Phillips Irrevocable Trust, Charlotte, NC (US)

(72) Inventors: Brian S. Phillips, Charlotte, NC (US); Adam T. Walsh, Charlotte, NC (US)

(73) Assignee: Phillips Irrevocable Trust, Charlotte, NC (US)

( * ) Notice: Subject to any disclaimer, the term of this patent is extended or adjusted under 35 U.S.C. 154(b) by 1228 days.

(21) Appl. No.: 17/681,692

(22) Filed: Feb. 25, 2022

(65) Prior Publication Data

US 2022/0310251 A1 Sep. 29, 2022

Related U.S. Application Data

(60) Provisional application No. 63/166,169, filed on Mar. 25, 2021.

(51) Int. Cl.
*G16H 40/67* (2018.01)

(52) U.S. Cl.
CPC .................................. *G16H 40/67* (2018.01)

(58) Field of Classification Search
CPC ...................................................... G16H 40/67
See application file for complete search history.

(56) References Cited

U.S. PATENT DOCUMENTS

| | | | | |
|---|---|---|---|---|
| 10,395,769 B2 * | 8/2019 | Ribble | .................. | A61B 90/90 |
| 10,535,995 B2 * | 1/2020 | Kawata | ............... | H04L 12/2829 |
| 2004/0138920 A1 * | 7/2004 | Sawanaga | .............. | G16H 40/20 702/182 |

(Continued)

FOREIGN PATENT DOCUMENTS

| | | | | |
|---|---|---|---|---|
| EP | 1623666 A2 | 2/2006 | | |
| WO | WO2005/022692 A2 | 3/2005 | | |
| WO | WO-2015074007 A1 * | 5/2015 | ........... | G08B 21/043 |

OTHER PUBLICATIONS

WO-2015074007-A1_translated (Year: 2015).*

(Continued)

*Primary Examiner* — Catherine T. Rastovski
*Assistant Examiner* — Michael J Singletary
(74) *Attorney, Agent, or Firm* — Morgan, Lewis & Bockius LLP

(57) ABSTRACT

This application is directed to a centralized power data management system for managing power data of remote medical devices located at one or more medical facilities. A server is communicatively coupled to a plurality of power cables. Each power cable includes a cord device and is electrically coupled to, and configured to power, a respective medical device. A power profile is received from a first cord device of a first power cable and includes power data characteristics measuring power delivered to a first medical device while the first medical device conducts a medical procedure. The power profile is used to identify the conducted medical procedure, including one or more numeric operational parameters of the medical procedure. The computer system sends a message associated with the conducted medical procedure to a second electronic device for display on a user interface of the second electronic device.

20 Claims, 16 Drawing Sheets

(56) References Cited

U.S. PATENT DOCUMENTS

| | | | | |
|---|---|---|---|---|
| 2010/0082174 | A1* | 4/2010 | Weaver | F24F 11/46 700/295 |
| 2016/0359325 | A1* | 12/2016 | Kawata | H04L 12/2829 |
| 2020/0294649 | A1* | 9/2020 | Pabla | G16H 20/60 |
| 2022/0223269 | A1* | 7/2022 | Masson | G16H 40/20 |

OTHER PUBLICATIONS

Office Action dated Sep. 23, 2024, issued in corresponding European Patent Application No. 22710894.1.

Phillips Irrevocable Trust, International Search Report and Written Opinion, PCT/US2022/018223, May 18, 2022, 23 pages.

Naguib et al., "A Novel Technique To Monitor Medical Equipment Modes of Operation", Jes, Assiut University, Faculty of Engineering, vol. 47, No. 6, Nov. 2019, pp. 783-794.

Office Action dated Mar. 19, 2026, issued in corresponding Chinese Patent Application No. 202280037729.9.

* cited by examiner

SMART CORDS IN MEDICAL APPLICATIONS

RELATED APPLICATION

This application claims priority to U.S. Provisional Patent Application No. 63/166,169, titled "Smart Cords in Medical Applications," filed on Mar. 25, 2021, which is hereby incorporated by reference in its entirety.

TECHNICAL FIELD

The present application generally relates to a centralized power management system that gathers, analyzes, and reports power usage characteristics of distributed medical devices that are powered via power cables.

BACKGROUND

Medical devices are distributed across different medical facilities and often operate independently of other medical devices. Some medical device manufacturers provide a medical device usage platform to collect usage characteristics of medical devices distributed across different medical facilities. However, such a device usage platform is often limited to one or more specific types of medical devices provided by the same manufacturer and relies on direct communication with those medical devices. The usage characteristics are preferably collected and transferred to the device usage platform after the medical procedures are completed, because real-time data communication consumes local resources, creates a tampering risk to the ongoing medical procedures, and can compromise performance of the medical procedures. However, such delayed data transfer is easily neglected or interrupted and does not address a concern of leaking privacy-sensitive patient information stored on the medical devices.

SUMMARY

It is beneficial to develop a centralized data management mechanism to manage usage characteristics of different types of distributed medical devices in a secure and efficient manner.

The present application describes embodiments related to using a smart cord device between a power outlet and a medical device to gather and report device usage characteristics related to the medical device while providing power to the medical device. The smart cord device is part of a medical grade power cable configured to operate at a gauge in compliance with specifications of the medical device. Additionally, the smart cord device has one or more processors and memory storing instructions, which are executed by the processors to gather power profiles (e.g., power, voltage, and current of the medical device) and report them to a centralized power data management platform. The platform applies a data analysis algorithm (e.g., including a deep learning technique) to understand the power profiles gathered from one or multiple medical devices and translates the power profiles into digestible information about the medical devices and related medical procedures for an interested party. Specifically, the platform determines a range of device usage parameters and identifies device modes or operational states of the medical devices based on the gathered power profiles. Data is communicated between the smart cord devices and the centralized power data management platform via a secure and encrypted network (e.g., a private cellular network) without involving the medical devices or impacting operation of the related medical procedures.

In one aspect, a data management method is implemented at a server system hosting a centralized power data management system for a plurality of remote medical devices located at one or more medical facilities. The method includes communicatively coupling to a plurality of power cables via one or more wide area networks (WANs). Each of the power cables includes a cord device (i.e., a smart cord device having one or more processors and memory). Each power cable is electrically coupled to, and configured to power, a respective one of the plurality of remote medical devices. The plurality of remote medical devices includes a first medical device powered by a first power cable including a first cord device. The method further includes receiving a power profile from the first cord device of the first power cable. The power profile includes a plurality of power data characteristics measuring power delivered to the first medical device while the first medical device conducts a medical procedure. The method further includes using the power profile to identify the conducted medical procedure, including one or more numeric operational parameters of the conducted medical procedure, and sending a message to a second electronic device for display on a user interface of the second electronic device. The message specifies the conducted medical procedure and the one or more numeric operational parameters. In some embodiments, the second electronic device is the same as the first medical device. In some embodiments, the second electronic device is distinct from the first medical device.

According to another aspect of the present application, a computer system (e.g., a server system) includes one or more processing units, memory and a plurality of programs stored in the memory. The programs, when executed by the one or more processing units, cause the computer system to perform the method for managing data for medical devices as described above.

According to another aspect of the present application, a non-transitory computer readable storage medium stores a plurality of programs configured for execution by a computer system having one or more processing units. The programs, when executed by the one or more processing units, cause the computer system to perform the method for managing data for medical devices as described above.

BRIEF DESCRIPTION OF DRAWINGS

The accompanying drawings, which are included to provide a further understanding of the embodiments and are incorporated herein and constitute a part of the specification, illustrate the described embodiments and together with the description serve to explain the underlying principles.

Like reference numerals refer to corresponding parts throughout the several views of the drawings.

DETAILED DESCRIPTION

Reference will now be made in detail to specific embodiments, examples of which are illustrated in the accompanying drawings. In the following detailed description, numerous non-limiting specific details are set forth in order to assist in understanding the subject matter presented herein. But it will be apparent to one of ordinary skill in the art that various alternatives may be used without departing from the scope of claims and the subject matter may be practiced without these specific details. For example, it will be apparent to one of ordinary skill in the art that the subject matter presented herein can be implemented on many types of electronic devices with digital video capabilities.

Various embodiments of this application are directed to a centralized power data management platform communicatively coupled to a plurality of power cord devices and configured to collect power usage characteristics of medical devices via these power cord devices while or after the medical devices implement medical procedures. Each power cord device is part of a power cable connecting a respective medical device to a power outlet. Such a power cord device facilitates powering the respective medical device, and generally does not exchange data directly with the medical device via the power cable. When a medical procedure is implemented by the medical device, the power cord device generally does not have an access to data stored in the medical device. However, the power cord device can monitor the power usage characteristics associated with the medical procedure (i.e., a power profile including instantaneous current or power provided by the power cable to enable the medical procedure) without knowing what kind of medical device or what type of medical procedure has been powered by the power cable. The centralized power data management platform can collaborate with the power cord devices to collect the power usage characteristics from different types of medical devices and in association with different types of medical procedures, analyze the collected power usage characteristics, generate analysis results (e.g., statistics of medical devices, users, treatment settings, procedure time, and geographical distribution), and provide the analysis results to a user of its data service.

Additionally, in some embodiments, firmware running on a power cord's CPU/processor knows some characteristics of a medical device powered by the power cord. The power cord is configured to classify power events locally instead of determining treatment characteristics entirely on a remote power cord server. In some situations, this power cord would need firmware specific to its cord device to properly classify power events.

Figure 1:
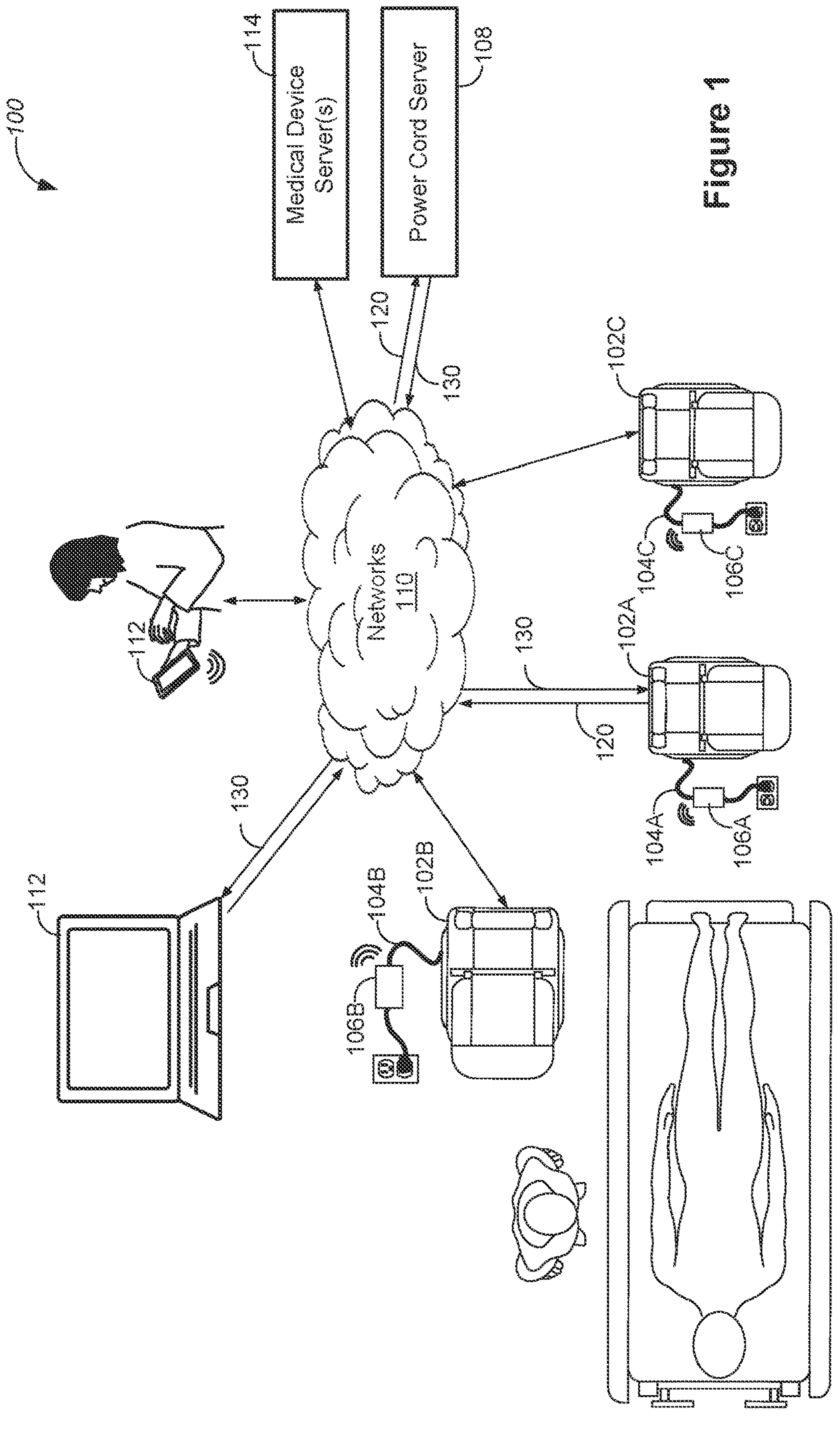
FIG. 1 is an example data management environment for a plurality of medical machines or devices, in accordance with some embodiments.

FIG. 1 is an example data management environment 100 for a plurality of medical machines or devices 102, in accordance with some embodiments. Each medical machine or device 102 (also simplified as medical device 102) is configured to implement one or more respective specialized medical procedures. Examples of the medical procedures include, but are not limited to, computed tomography (CT scan), radiography, magnetic resonance imaging (MRI scan), ultrasound, endoscopy, echocardiogram (EKG or ECG), intravenous, epidural or arterial infusion, LASIK surgery, non invasive aesthetic, invasive aesthetic surgeries, and laser surgery. Examples of the medical devices 102 include, but are not limited to, kidney machine, ventilator, cardiopulmonary bypass device (i.e., heart-lung machine), dialysis machine, incubator, various laser machines, various gas machines, various medical imaging machines, and various medical laboratory equipment. Each medical device 102 is connected to a power outlet via a power cable 104 including a power cord device 106 and two cable portions extending from two ends of the power cord device 106, and the power cable 104 provides power to the medical device 102. In some embodiments, the power cable 104 including the power cord device 106 does not provide data to or receive data from the medical device 102. Conversely, in some embodiments, the power cord device 106 provides data to or receives data from the medical device 102 wirelessly (e.g., using near field communication (NFC) or Bluetooth communication) or via a wire (e.g., via a cable portion of the corresponding power cable 104). It is noted that the same type of power cables 104 or the same type of power cord devices 106 may be used with different types of medical devices 102.

The power cord devices 106 are communicatively coupled to a power cord server 108 (also called a smart cord server 108) via one or more communication networks 110. While a medical device 102 implements a medical procedure, the corresponding power cord device 106 connected to the medical device 102 records a power profile 120 including a plurality of power data characteristics measuring power delivered to the medical device 102, and reports the power profile 120 to the power cord server 108 via the one or more communication networks 110. In some embodiments, the power cord device 106 reports the power profile 120 in real time while the medical procedure is being implemented. In some embodiments, the power cord device 106 reports the power profile 120 after each medical procedure is completed. In some embodiments, the power cord device 106 reports a batch of power profiles 120 including one or more power profiles 120 according to a predefined reporting schedule or periodically. In some embodiments, each power cord device 106 is communicatively coupled to the power cord server 108 via a cellular network that does not need to be commissioned with any local area network. In this case, it is configured to report data (e.g., the power profiles 120) to the power cord server 108 without or with little user intervention once the power cord device 106 is connected to the corresponding medical device 102.

The power cord server 108 enables the centralized data management platform to manage the power profiles 120 collected in association with the plurality of medical devices 102, which may include more than one device type. After collecting the power profiles 120 from multiple power cord devices 106, the power cord server 108 analyzes the power profiles 120 to identify medical procedures conducted by these medical devices 102, including one or more numeric operational parameters, device modes, and/or operational states of the conducted medical procedure, and may even generate statistics of these medical procedures. The power cord server 108 then generates a message 130 to report the medical procedures with the one or more numeric operational parameters to a medical device 102 or client device 112 for display on a user interface of the medical device 102 or client device 112. In some embodiments, the message 130 includes a summary of the statistics of the medical procedures monitored by more than one medical device 102, and the client device 112 receiving the message 130 may visualize the statistics on its user interface.

In some embodiments, a cord device 106 pre-processes the power profile 120 collected in association with a connected medical device 102. Firmware running on the cord device 106 recognizes some data characteristics of the medical device 102 powered by the corresponding power cord 104. The cord device 106 is configured to identify a device type, device mode, operational state, medical procedure, or power events locally instead of determining treatment characteristics entirely on the power cord server 108. The pre-processed power profile 120 is provided by the power cord server 108 for further profile processing and/or generating the message sent to other medical or client devices using this cord data service. In some embodiments, the cord device 106 is a specialized cord device including a hardware or software module that is configured to identify information associated with one or more specific types of medical device 102.

In some embodiments, the power cord server 108 is configured to support a power cord application (e.g., applications 634A and 634B in FIGS. 6A and 6B), which is executed at medical devices 102 or at client devices 112 and configured to enable the user interface for displaying information contained in the message 130. The power cord application may be a browser-based application or a dedicated data application. The user interface is configured to receive a user query and present the information contained in the message 130 according to the user query. The message may include an alert, a notification, a report, and/or an instruction concerning the medical procedures.

In some embodiments, when a power cord device 106 is connected to a respective medical device 102, the type of the respective medical device 102 is not communicated or known to the power cord device 106. Likewise, in some embodiments, when the power cord device 106 reports a power profile 120 concerning a medical procedure of the respective medical device 102, the type of the medical procedure is not communicated or known to the power cord device 106. In some embodiments, the power cord device 106 identifies one or more power features in each power profile 120, derives a type of the medical device 102 and/or medical procedure based on the identified power features, and reports the types of the medical device 102 and/or medical procedure with the power profile 120 to the power cord server 108. Alternatively, in some embodiments, the power cord server 108 is configured to identify one or more power features in each power profile 120 collected from the cord device 106 and derive the type of the medical device 102 and/or medical procedure based on the identified power features in the power profile 120. In some embodiments, the power cord device 106 or the power cord server 108 is configured to determine the type of the medical device 102 and/or medical procedure based on the power profile 120 and/or the corresponding power features using deep learning techniques.

In some embodiments, a medical device 102 operates offline and is isolated from any communication network 110 (e.g., for the purposes of maintaining data security and privacy). The medical device 102 is configured to execute a medical device application (e.g., the application 630A in FIG. 6A) locally. Alternatively, in some embodiments, a medical device 102 is communicatively coupled to a respective medical device server 114 via the one or more communication networks 110 (e.g., during a medical procedure or only when no medical procedure is being performed). The same type of medical devices are coupled to the same medical device server 114. Different types or brands of medical devices are coupled to distinct medical device server 114. Each medical device server 114 or medical device 102 may operate independently of the power cord server 108 and has no knowledge of the existence of the power cord device 106. Conversely, in some situations, the medical device server 114 or medical device 102 interacts with the power cord server 108. The medical device 102 is configured to execute a medical device application (e.g., the application 630A in FIG. 6A) jointly with the respective medical device server 114 for the purposes of controlling the medical device 102 to implement the medical procedure. Under some circumstances, this medical device application is also configured to receive the message 130 concerning a medical procedure conducted by this medical device 102 or other medical devices 102 from the power cord server 108, and display the message 130 on its user interface. In an example, the user interface of the medical device application includes an embedded window or a popup window for displaying the message 130 provided by the power cord server 108.

The data management environment 100 further includes a plurality of client devices 112 communicatively coupled to at least the power cord server 108. Each client device 112 may be, for example, a desktop computer, a tablet computer, or a mobile phone. Each client device 112 can collect data or user inputs, execute user applications (e.g., the power cord application 634B in FIG. 6B), or present outputs on its user interface. The collected data or user inputs can be processed locally at the client device 112 and/or remotely by the server(s) 108 or 114. The servers 108 and 114 provide system data (e.g., boot files, operating system images, and user applications) to the client devices 112, and in some embodiments, process the data and user inputs received from the client device(s) 112 when the user applications are executed on the client devices 112. In an example, a client device 112 communicates with a medical device server 114 and is used to remotely control a medical procedure implemented by a medical device 102 coupled to the medical device sever 114. In another example, a client device 112 communicates with the power cord server 108 and controls collection, analysis and reporting of power usage characteristics of the medical devices 102.

The servers 108 and 114, the client devices 112, the cord devices 106, and the medical devices 102 (if any) are communicatively coupled to each other via one or more communication networks 110, which are the medium used to provide communications links between these devices and computers connected together within the data management environment 100. The one or more communication networks 110 may include connections, such as wire, wireless communication links, or fiber optic cables. Examples of the one or more communication networks 110 include local area networks (LAN), wide area networks (WAN) such as the Internet, or a combination thereof. The one or more communication networks 110 can be implemented using any known network protocol, including various wired or wireless protocols, such as Ethernet, Universal Serial Bus (USB), FIREWIRE, Long Term Evolution (LTE), Global System for Mobile Communications (GSM), Enhanced Data GSM Environment (EDGE), code division multiple access (CDMA), time division multiple access (TDMA), Bluetooth, Wi-Fi, voice over Internet Protocol (VoIP), Wi-MAX, or any other suitable communication protocol. A connection to the one or more communication networks 110 may be established either directly (e.g., using 3G/4G/5G connectivity to a wireless carrier), or through a network interface (e.g., a router, switch, gateway, hub, or an intelligent, dedicated whole-home control node), or through any combination thereof. The one or more communication networks 110 can represent the Internet of a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages 130. In some embodiments, all power cord devices 106 are communicatively coupled to the power cord server 108 via a secure and encrypted private cellular network, and configured to report data to the power cord server 108 independently of any local wired or wireless network after the power cord devices 106 are connected to the medical devices 102.

In some embodiments, deep learning techniques are applied in the data management environment 100 to process the power profiles 120 collected by the power cord devices 106 (e.g., to identify power features and operational parameters contained in the power profiles 120, identify new device modes, operational states and medical procedures, match the power profiles 120 with medical procedures, categorize the power profiles 120, and/or synthesize related power characteristics). In these deep learning techniques, data processing models are created based on one or more neural networks to process the power profiles 120. These data processing models may be trained with training data before they are applied to process the power profiles 120. Both model training and data inference are implemented at the power cord server 108, and results (e.g., the messages 130) are reported to individual client devices 112 or medical devices 102 for review by a user of data management service provided by this data management environment 100.

Figure 2A:
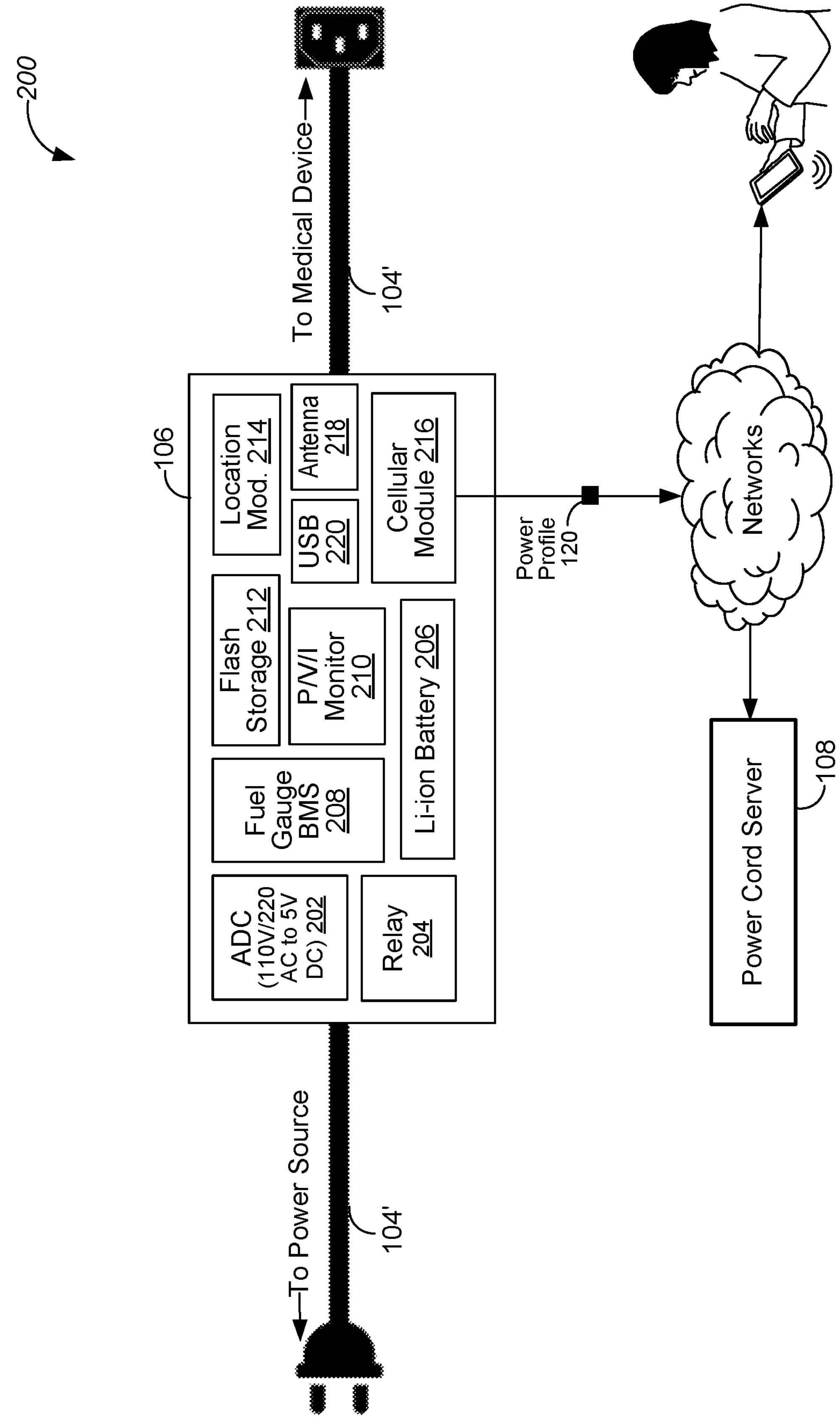
FIG. 2A is an example operational environment for a power cord device of a power cable, in accordance with some embodiments.
Figure 2B:
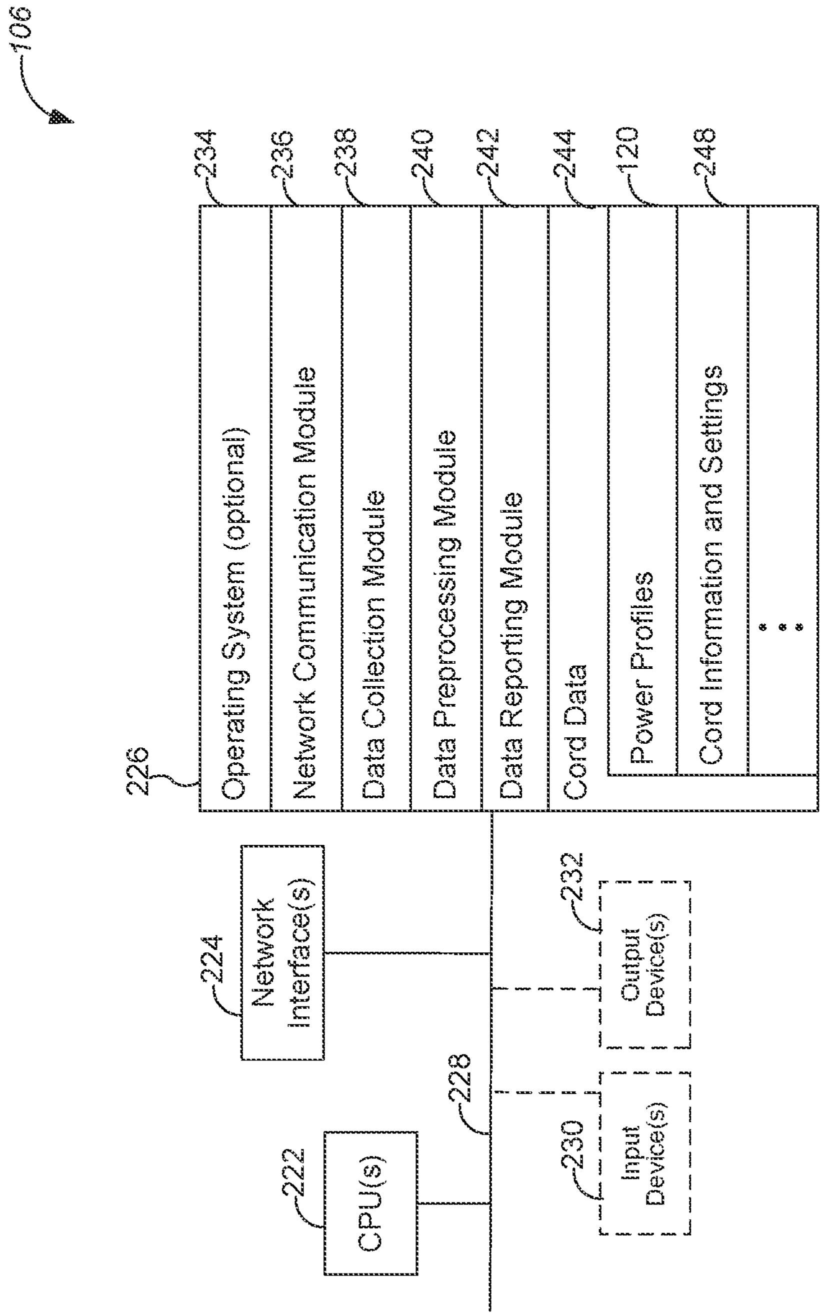
FIG. 2B is a block diagram of a power cord device, in accordance with some embodiments.

FIG. 2A is an example operational environment 200 for a power cord device 106 of a power cable 104, in accordance with some embodiments, and FIG. 2B is a block diagram of a power cord device 106, in accordance with some embodiments. Two ends of the power cable 104 are configured to be connected to a power source (e.g., a standard wall socket) and a medical device 102, respectively. The power cord device 106 is coupled to the power cable 104, and configured to monitor power as the power cable 104 transfers the power from the power source to the medical device 102. The power cable 104 includes two cable portions 104' extending from two ends of the power cord device 106. The power is recorded as a power profile 120 (e.g., the current flow is sampled at a predefined sample rate) and reported to and analyzed by a power cord server 108. Analysis results (e.g., messages 130) are then presented to a user on a user interface of a client device 112 or medical device 102.

In some embodiments, the power cord device 106 is utilized to gain insight into devices usage patterns, treatment settings, physical location, and other characteristics of the medical device 102. The power cord server 108 learns how the power profile 120 matches to a treatment setting or device mode on the medical device 102, and translates the power profile 120 of the medical device 102 into logical data presented in visual reports. In some embodiments, the power cord server 108 is configured to recognize power patterns associated with each medical procedure of different medical devices (e.g., using deep learning techniques). In some embodiments, the power cord server 108 is configured to remotely manage software components that manipulate, batch, sort, and initiate transmission of data ingested from microprocessors of the power cord device 106. In some embodiments, the power cord server 108 includes a machine learning component to categorize characteristics of data across a device type and determine that additional power cord devices 106 are added into the data management environment 100. In some embodiments, the power cord device 106 or power cord server 108 is installed with a proprietary software program to map unique power usage characteristics to device type, device mode, operational state and settings of medical procedures (e.g., using deep learning techniques). In some embodiments, a website platform is deployed to display, sort, correlate, and export post-processed and interpreted data provided by the power cord server 108.

Referring to FIG. 2A, the power cord device 106 includes one or more of: an AC-to-DC converter (ADC) 202, a relay 204, a battery 206, a battery management system (including a fuel gauge) 208, a power monitor module 210, flash storage 212, a location module 214, a cellular module 216, an antenna 218, and a connector 220. The ADC 202 is configured to convert an AC supply voltage provided by the power source to a DC supply voltage for powering operation of the power cord device 106. The relay 204 is configured to receive a control or instruction and enable/disable the power flow to the medical device 102 or the power cord device 106 (e.g., an emergency shut-off). This control or instruction can be provided remotely by the power cord server 108. The battery 206 is controlled by the battery management system 208 to store power. The location module 214 is configured to identify the geographical location of the power cord device 106, and can be a global positioning system (GPS) or other module capable of providing geolocation information. In an example, a location of the cord device 106 is determined based on a WiFi basic service set identifier (BSSID) or received signal strength indicator (RSSI). The power monitor module 210 is configured to sample power, voltage, or current values related to usage of the medical device 102. Such sampled values form the power profile 120 of the medical device 102, and are digitalized and stored temporarily in the flash memory 212. The power profile 120 stored in the flash memory 212 is transferred to the power cord server 108 via the one or more communication networks 110. In an example, the power profile 120 is transferred in an encrypted HIPAA compliant format over a private cellular network (e.g., using the cellular module 216). In another example, the power profile 120 is transferred with information of the geographical location of the power cord device 106.

Referring to FIG. 2B, in some embodiments, the power cord device 106 includes one or more processors 222 and memory 226 storing instructions to be executed by the processor(s) 222 to monitor, store, preprocess, and/or transmit collected power profiles. The power cord device 106 further includes one or more network interfaces 224, memory 226, and one or more communication buses 228 for interconnecting these components (sometimes called a chipset). In some embodiments, the power cord device 106 includes one or more input devices 230 that facilitate user input, such as a touch screen display, a touch-sensitive input pad, or other input buttons or controls. In some embodiments, the power cord device 106 includes one or more output devices 232 that enable presentation of user interfaces and display content, including one or more visual displays and light indicator.

Memory 226 includes high-speed random access memory, such as DRAM, SRAM, DDR RAM, or other random access solid state memory devices. In some embodiments, the memory includes non-volatile memory, such as one or more magnetic disk storage devices, one or more optical disk storage devices, one or more flash memory devices, or one or more other non-volatile solid state storage devices. In some embodiments, the memory 226 includes one or more storage devices remotely located from one or more processing units 222. The memory 226, or alternatively the non-volatile memory within the memory 226, includes a non-transitory computer readable storage medium. In some embodiments, the memory 226, or the non-transitory computer readable storage medium of the memory 226, stores the following programs, modules, and data structures, or a subset or superset thereof:

- an operating system 234, including procedures for handling various basic system services and for performing hardware dependent tasks;
- a network communication module 236, which connects each power cord device 106 to the power cord server 108 via one or more network interfaces 224 (wired or wireless) and one or more communication networks 110, such as a private and encrypted cellular network;
- a data collection module 238, which collects power profiles 120, including a plurality of power data characteristics measuring power delivered to a medical device coupled to the power cord device 106;
- a data preprocessing module 240, which processes the collected power profiles 120. In some embodiments, a recognition method is applied to identify a device type of a medical device 102 and/or a device mode, an operational mode, and/or a medical procedure of the medical device 102, based on a power profile 120;
- a data reporting module 242, which reports the collected or preprocessed power profiles 120 (e.g., in real time, periodically, or according to a predefined reporting schedule); and
- one or more databases 244, which store cord data, including one or more of:
  - power profiles 120, which are captured by the power monitor module 210 and preprocessed; and
  - cord information and settings 248, including common device settings (e.g., serial identification, geographical location, service tier, device model, storage capacity, processing capabilities, communication capabilities, etc.) of the power cord device 106.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, modules or data structures, and thus various subsets of these modules may be combined or otherwise re-arranged in various embodiments. In some embodiments, the memory 226 stores a subset of the modules and data structures identified above. In some embodiments, the memory 226 stores additional modules and data structures not described above.

Figure 3:
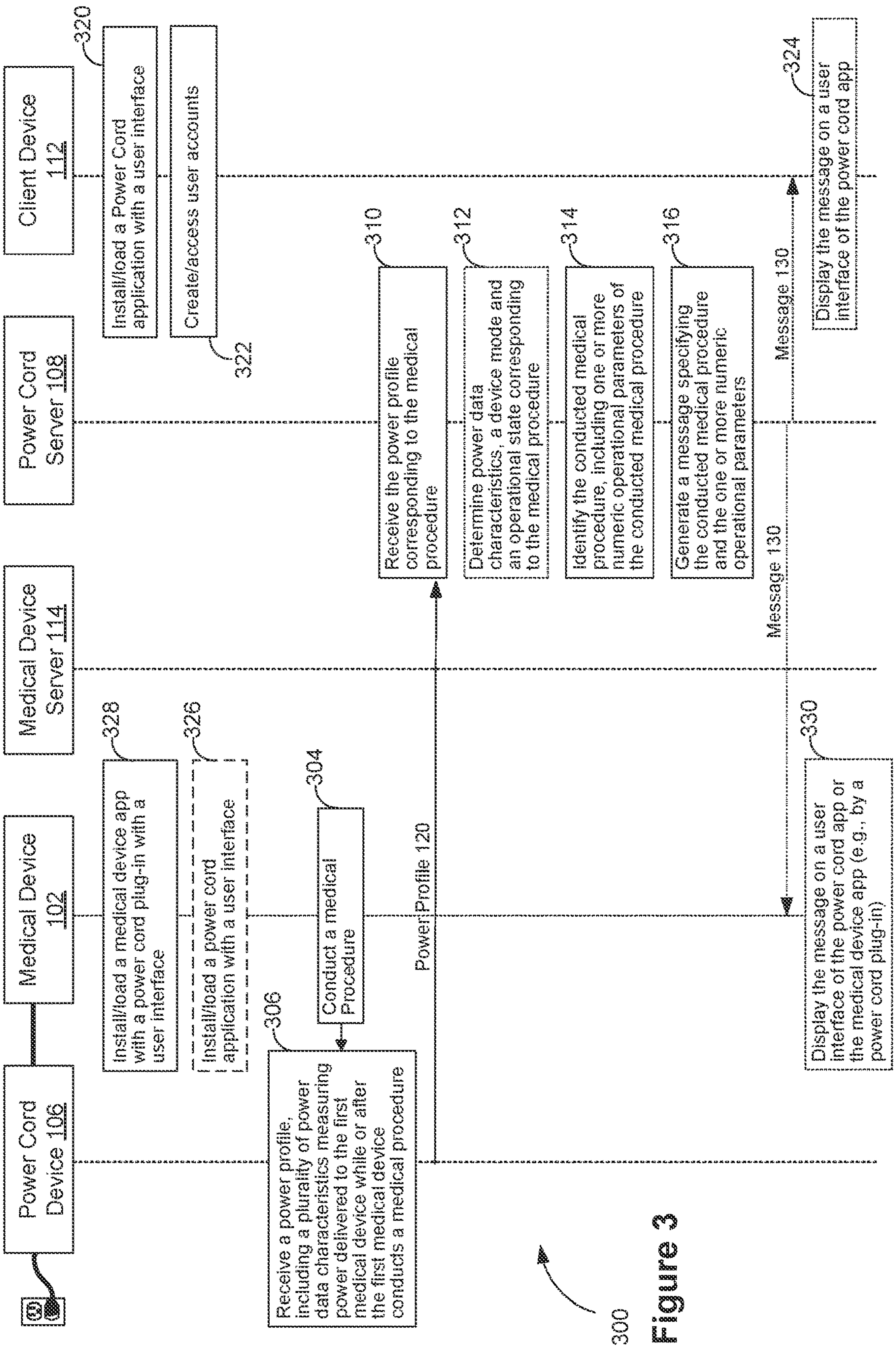
FIG. 3 is a flow diagram of an example process of managing power data for a medical device 102, in accordance with some embodiments.

FIG. 3 is a flow diagram of an example process 300 of managing power data for a medical device 102, in accordance with some embodiments. The process 300 is implemented jointly by a power cord device 106, a power cord server 108, and an electronic device (e.g., a medical device 102 or a client device 112). The medical device 102 is connected to a power source by a power cable 104 including the power cord device 106. The medical device 102 has a device mode (e.g., an operation mode and an idle mode). The medical device 102 is configured to conduct one or more types of medical procedures in the operation mode based on treatment settings and switch to the idle mode after a medical procedure or a batch of consecutive medical procedures have been performed. The medical device 102 includes one or more processors and memory storing instructions to be executed by its processors. Specifically, the medical device 102 is installed (328) with a medical device application (e.g., the application 630 in FIG. 6A), which is loaded to control each medical procedure based on the corresponding treatment settings. In some embodiments, a power cord application is also installed (326). While the medical device 102 is conducting (304) the medical procedure, the power cord device 106 records (306) power data characteristics associated with the medical procedure in real time according to a sample rate. The recorded power data characteristics measure power delivered to the medical device 102 while the medical device 102 conducts the medical procedure and forms a power profile 120 of the medical device 102.

The power cord device 106 reports the power profile 120 corresponding to the medical procedure to the power cord server 108, while the medical procedure is being performed or after the medical procedure is completed. After receiving (310) the power profile 120, the power cord server 108 analyzes the power data characteristics of the power profile and determines (312) whether each portion or interval of the power profile is associated with the operation mode or the idle mode of the medical device 102. The power cord server 108 identifies (314) the conducted medical procedure, including one or more numeric operational parameters of the conducted medical procedure in the power profile 120. For example, a specific type of medical procedure has one or more power features (e.g., a train of power pulses), and the power cord server 108 identifies the numeric operational parameters corresponding to the power features of the medical procedure in the power profile (e.g., a frequency, power pattern, and average power peak of the train of power pulses). Based on the numeric operational parameters, it is thereby determined that the medical procedure of the specific type has been implemented by the medical device 102 connected to the power cord device 106 that reports the power profile 120. In some embodiments, the power cord server 108 therefore generates (316) a message 130 specifying the conducted medical procedure and the one or more numeric operational parameters, and sends the message 130 to an electronic device for display on a user interface of the electronic device.

In some embodiments, the electronic device receiving the message 130 from the power cord sever 108 is a client device 112. The client device 112 is installed with and executes (320) a power cord application (e.g., the application 634B in FIG. 6B), which may be a browser-based application or a dedicated data application. User accounts are created (322) in the power cord application for users of data service provided by the power cord server 108. The user interface is displayed on the client device 112 via the power cord application to share the message 130 with the users of data service. The message 130 is displayed (324) on the user interface of the power cord application.

Alternatively, in some embodiments, the electronic device receiving the message 130 from the power cord sever 108 is a medical device 102 that is the same medical device 102 implementing the medical procedure or a distinct medical device 102. In some embodiments, the medical device 102 is installed with and executes (326) a power cord application (e.g., the application 634A in FIG. 6A), which may be a browser-based application or a dedicated data application, and user accounts are created in the power cord application for users of data service provided by the power cord server 108. In some embodiments, the medical device 102 is installed with and executes (328) a medical device application (e.g., the application 630A in FIG. 6A) for executing medical procedures using the medical device 102, and the medical device application includes a power cord plug-in program (e.g., the program 632A in FIG. 6A). The user interface presenting the message 130 is displayed (330) on the medical device 102 via the power cord application directly or via the power cord plug-in program of the medical device application.

It is noted that in some embodiments, firmware running on a cord device 106 recognizes some data characteristics of the medical device 102 powered by the corresponding power cord 104. The cord device is configured to identify a device type, device mode, operational state, medical procedure, or power events locally instead of determining treatment characteristics entirely on a remote power cord server 108. That said, a subset of the operations 312 and 314 can be implemented locally at the power cord device 106. Particularly, the cord device 106 can be customized with a hardware or software module to serve a specific type of medical device 102. As such, in various embodiments of this application, the operations 312 and 314 are optionally implemented entirely by the power cord device 106, entirely by the power cord server 108, or jointly by the cord device 106 and cord server 108.

Figure 4A:
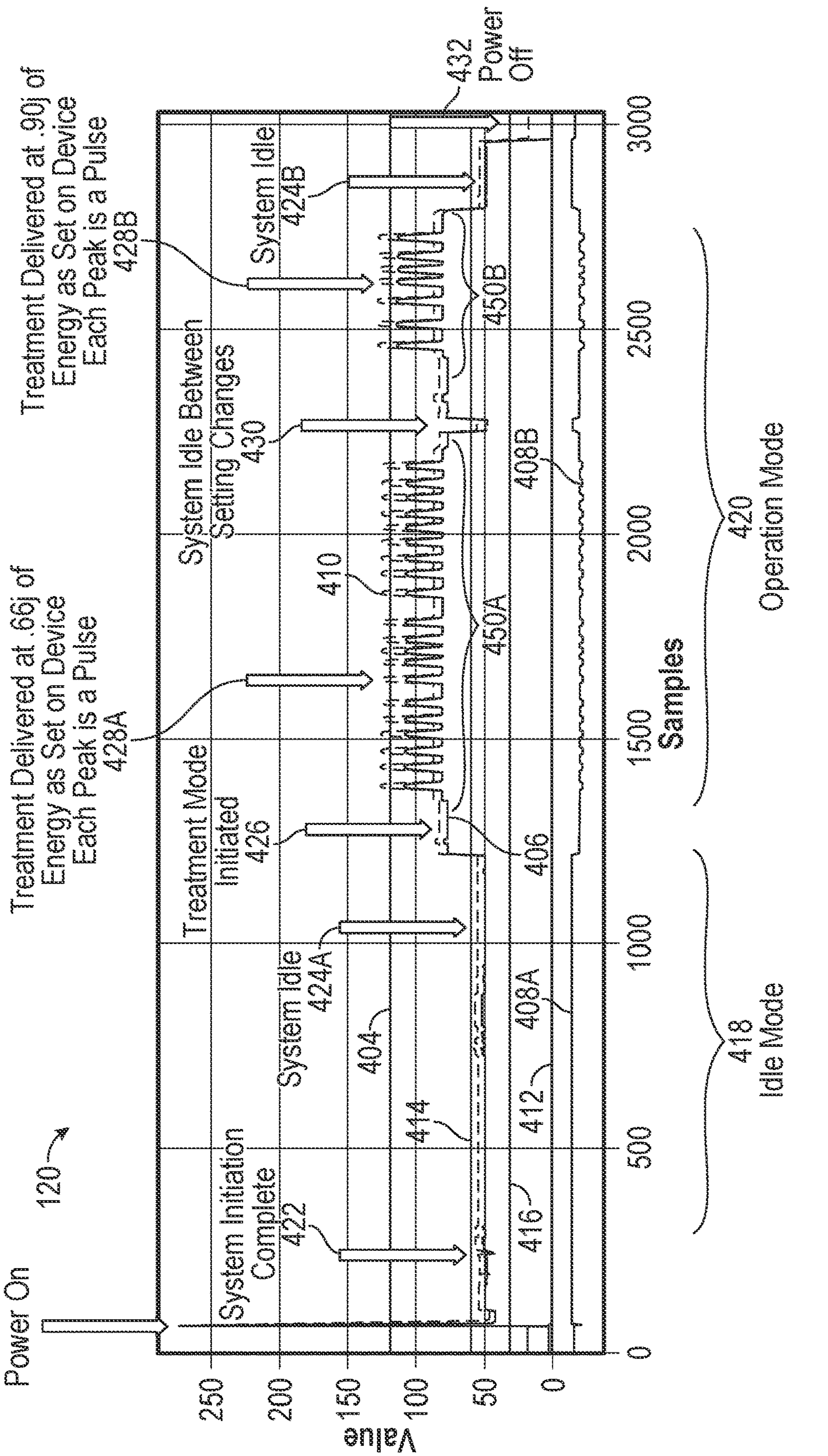
FIG. 4A is an example power profile collected from a power cord device 106, in accordance with some embodiments.
Figure 4B:
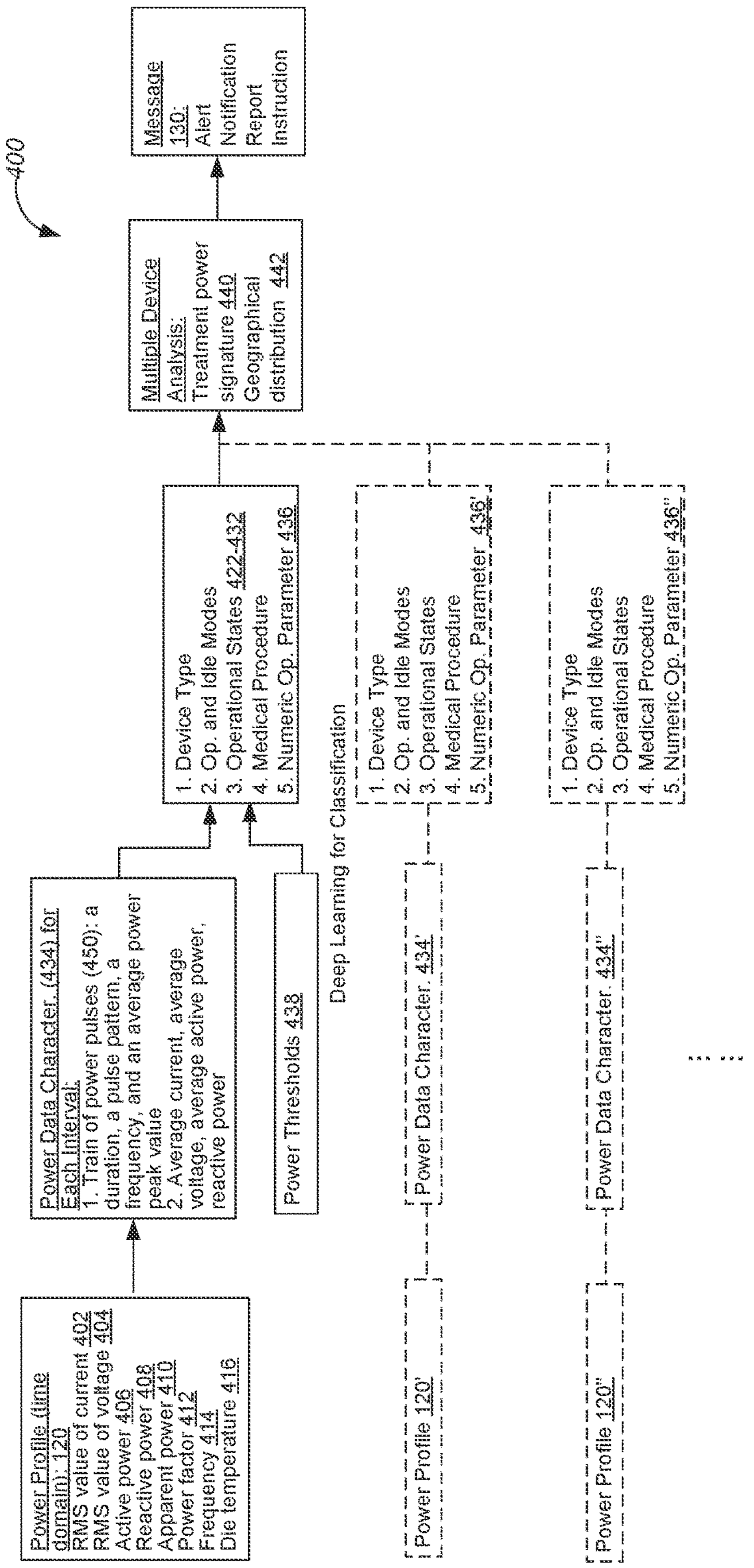
FIG. 4B is a flow of power data received, processed or generated by a power cord server, in accordance with some embodiments.

FIG. 4A is an example power profile 120 collected from a power cord device 106, in accordance with some embodiments, and FIG. 4B is a flow 400 of power data received, processed or generated by a power cord server 108, in accordance with some embodiments. This power profile 120 corresponds to a medical procedure implemented by an Ultherapy device manufacturer by Merz North America. This medical device 102 is powered on and delivers pulses from a transducer, and the pulses are applied to human tissue to tighten a corresponding tissue area by stimulating collagen creation. The power profile 120 includes a plurality of power parameters, including a root means square (RMS) value of current 402, an RMS value of voltage 404, an active power 406, a reactive power 408A and 408B, an apparent power 410, a power factor 412, a frequency 414, and a die temperature 416. The plurality of power parameters 402-416 are plotted as functions of samples or time, and are optionally associated with a plurality of time stamps. For example, 3000 samples are recorded for each power parameter at a sample rate of 30 samples per minute. In some embodiments, the plurality of power parameters 402-416 are stored in an HTML file, and transferred from the power cord device 106 to the power cord server 108. A power cord application (e.g., the application 634C in FIG. 6C) is executed to open the HTML, file and visualize the power parameters 402-416, thereby allowing a user to manipulate the power parameters 402-416 (e.g., turning on or off each power parameter, or zooming in for a portion of the power profile).

A subset of the plurality of power parameters 402-416 are substantially stable. For example, the RMS value of voltage 404 is 120V. The frequency 414 is 60 Hz. The die temperature 416 is stabilized at about 30° C. It is noted that the power factor 412 is a ratio of an electrical power dissipated by the power cord device 106 to a product of the RMS values of current and voltage 402 and 404 (i.e., the power delivered to the medical device 102). The power factor 412 is approximately 0, which indicates that the power dissipated by the power cord device 106 is negligible compared with the power delivered to the medical device 102. Additionally, the reactive power 408 associated with a reactive load is smaller than the active power 406 or apparent power 410. When the medical device 102 has been powered up and no medical procedure is performed in the idle mode 418, the reactive power 408A is substantially stable (e.g., it has a temporal variation less than 5%). When the medical procedure is performed in the operation mode 420, the reactive power 408B increases slightly and has a negligible variation compared with trains of power pulses 450 observed on the active power 406 or apparent power 410.

The power profile 120 corresponds to a plurality of operational states including a subset of: a system idle state 424A and 424B, a system initiation state 422, a treatment initiation state 426, one or more treatment states 428A and 428B, a treatment idle state 430, and a power off state 432. The idle mode 418 of the medical device 102 includes the system idle states 424A and 424B, and the operation mode 420 of the medical device 102 corresponds to a sequence of the treatment initiation state 426, a first treatment state 428A, a treatment idle state 430, a second treatment state 428B. The medical procedure of the medical device 102 is identified when a subset of the plurality of operational states is identified. In this example of FIG. 4A, a specific medical procedure is identified in accordance with detection of an ordered sequence of the first treatment state 428A, the treatment idle state 430, and the second treatment state 428B. Further, the first and second treatment states 428A and 428B are identified in accordance with detection of the train of power pulses 450A and 450B, and the treatment idle state 430 is identified in accordance with a corresponding power drop and a location between the two trains of power pulses 450A and 450B. Given that a subset of the power parameters 402-416 are substantially stable, the medical procedure is determined based on at least one of remaining power parameters, such as the RMS value of current 402, active power 406, and apparent power 410, and the at least one of remaining power parameters is optionally processed using deep learning techniques to identify each of the states 428A, 430, and 428B, their corresponding ordered sequence, and/or the specific medical procedure.

The first treatment state 428A includes a train of power pulses 450A, which are characterized by power data characteristics 434 (see FIG. 4B) measuring power delivered to this medical device 102 while the medical device 102 conducts the corresponding medical procedure. A subset of these power data characteristics 434 are measured from the active power 406 and apparent power 410, and include the duration, the frequency, the power pattern, and the average power peak value of the train of power pulses 450A. The power cord server 108 identifies the first treatment state 428A based on the subset of power data characteristics 434 and determines the one or more numeric operational parameters 436 (see FIG. 4B) of the conducted medical procedure. In an example, the power pattern and frequency of the power pulses can be used to identify the first treatment state 428A and the corresponding medical procedure. The numeric operational parameters 436 of the medical procedure include the power level and the duration of the medical procedure, which are determined from the subset of power data characteristics 434, and sent to a user of the data service provided by the power cord server 108.

Additionally, in some embodiments, each of the plurality of operational states 422-432 is defined according to at least one power threshold 438 (see FIG. 4B) associated with a respective subset of the power data characteristics 434. The at least one power threshold 438 associated with each of the plurality of operational states 422-432 is determined and adjusted based on a deep learning technique. In some situations, the ordered sequence of states 426-430 in the operation mode 420 is initially unknown to the power cord system 108, and repeatedly appears in the power profiles collected from different medical devices 102. The power cord server 108 applies the deep learning technique to determine one or more power thresholds associated with each of the states in the sequence of states 426-430, recognizes the sequence of states 426-430, or classifies the sequence of states 426, 428A, 430, and 428B as the medical procedure.

The plurality of operational states 422-432 is ordered sequentially in the power profile 120. In some embodiments, after receiving the power profile 120, the power cord server 108 divides the power profile 120 into a plurality of power intervals. Each power interval corresponds to a respective one of the plurality of operational states 422-432. For each power interval, the power cord server 108 determines whether the respective power interval includes a train of power pulses 450 (e.g., using a deep learning technique). In accordance with a determination that the respective power interval includes a train of power pulses 450 (e.g., in the active power 406 of the first treatment state 428A), the power cord server 108 determines one or more of the duration, the pulse pattern, the frequency, and the average power peak value of the train of power pulses, as a respective subset of the power data characteristics 434 corresponding to the respective interval. Conversely, in accordance with a determination that the respective power interval does not include a train of power pulses 450, the power cord server 108 determines one or more of the average current, the average voltage, the average active power, and the reactive power, as the respective subset of the power data characteristics 434 corresponding to the respective interval. For example, a value of the reactive power 408A or 408B is a power data characteristic 434 that can be used to determine whether the medical device 102 operates in the idle mode 418 or operation mode 420.

In some embodiments, for each of the power intervals, the respective subset of the power data characteristics 434 corresponding to the respective interval is compared with at least a respective power threshold 438. In accordance with a determination that the comparison for a first power interval satisfies an association criterion of a first operational state 428A, the first operational state 428A is associated with the first power interval. The one or more numeric operational parameters 436 of the conducted medical procedure (e.g., the power level of the medical procedure) are determined based on the respective subset of the power data characteristics 434 corresponding to the first power interval (e.g., the frequency, power pattern, and average power peak value of the first power interval). Further, in some embodiments, the respective power threshold associated with the first operational state 428A is determined and adjusted based on a first deep learning technique.

Referring to FIGS. 1 and 4B, after the power profile 120 is received from a first power cord device 106A, the power data characteristics 434 are extracted and used to determine the type of the corresponding first medical device 102A, the device mode (i.e., an idle mode 418 or operation mode 420), each operational state associated with a respective power interval, the type of the medical procedure, and one or more first numeric operational parameters 436 of the medical procedure. When multiple power profiles 120 are received from more than one power cord device 106, the power cord server 108 analyzes the multiple power profiles 120 jointly and provides additional information that cannot be derived using a single power profile 120.

For example, in some embodiments, the power cord server 108 receives from a second cord device 106B of a second power cable 104B a second power profile 120' including a plurality of second power data characteristics 434' measuring power delivered to a second medical device 102B while the second medical device 102B conducts the same medical procedure. The second power profile 120' is used to identify one or more second numeric operational parameters 436' of the same medical procedure. The message 130 is generated based on the first and second numeric operational parameters 436 and 436' of the same medical procedure. In some embodiments, the message 130 reports a statistical analysis result of the numeric operational parameters 436 of a plurality of medical devices 102 including the first and second medical devices 102A and 102B. Further, in some embodiments, a treatment power signature 440 is determined for the same medical procedure based on at least the first and second numeric operational parameters 436 and 436', and the message 130 sent to another electronic device includes the treatment power signature 440. Examples of the treatment power signature include, but are not limited to, the most commonly used power data characteristics and the most effective power data characteristics for the medical procedure. Additionally, in some embodiments, the other electronic device receiving the message 130 from the power cord server 108 is configured to adjust a subsequent medical procedure implemented by the electronic device based on the treatment power signature 440 received in the message 130.

Alternatively, in some embodiments, the power cord server 108 receives a plurality of third power profiles 120" from a plurality of third power cables 106C. Each of the plurality of third power profiles 120" includes a respective plurality of third power data characteristics 434" measuring power delivered to a respective third medical device 106C while the respective third medical device 106C conducts a respective third medical procedure. Each of the plurality of third power profiles 120" is used to identify the respective third medical procedure, including one or more third numeric operational parameters 436" of the respective third medical procedure. The message 130 is generated based on the one or more first numeric operational parameters 436 of the conducted medical procedure and the third numeric operational parameters 436" corresponding to the plurality of third power profiles 120. For example, the message 130 may identify a most implemented medical procedure or an average procedure time for different medical procedures. In some embodiments, the first power profile 120 and the plurality of third power profiles 120" comply with a geographical or temporal limitation (e.g., directed to medical procedures in a geographical region and within a defined duration of time), and the message 130 is generated based on the geographical or temporal limitation. In an example, a geographical distribution 442 is obtained based on analysis of the power profiles 120 and 120" and sent with the message 130. In an example, the message 130 indicates that the most popular medical procedure is LASIK surgeries during a five-year period and that 23% of all medical procedures conducted in Florida during the five-year period are LASIK surgeries.

Figure 5A:
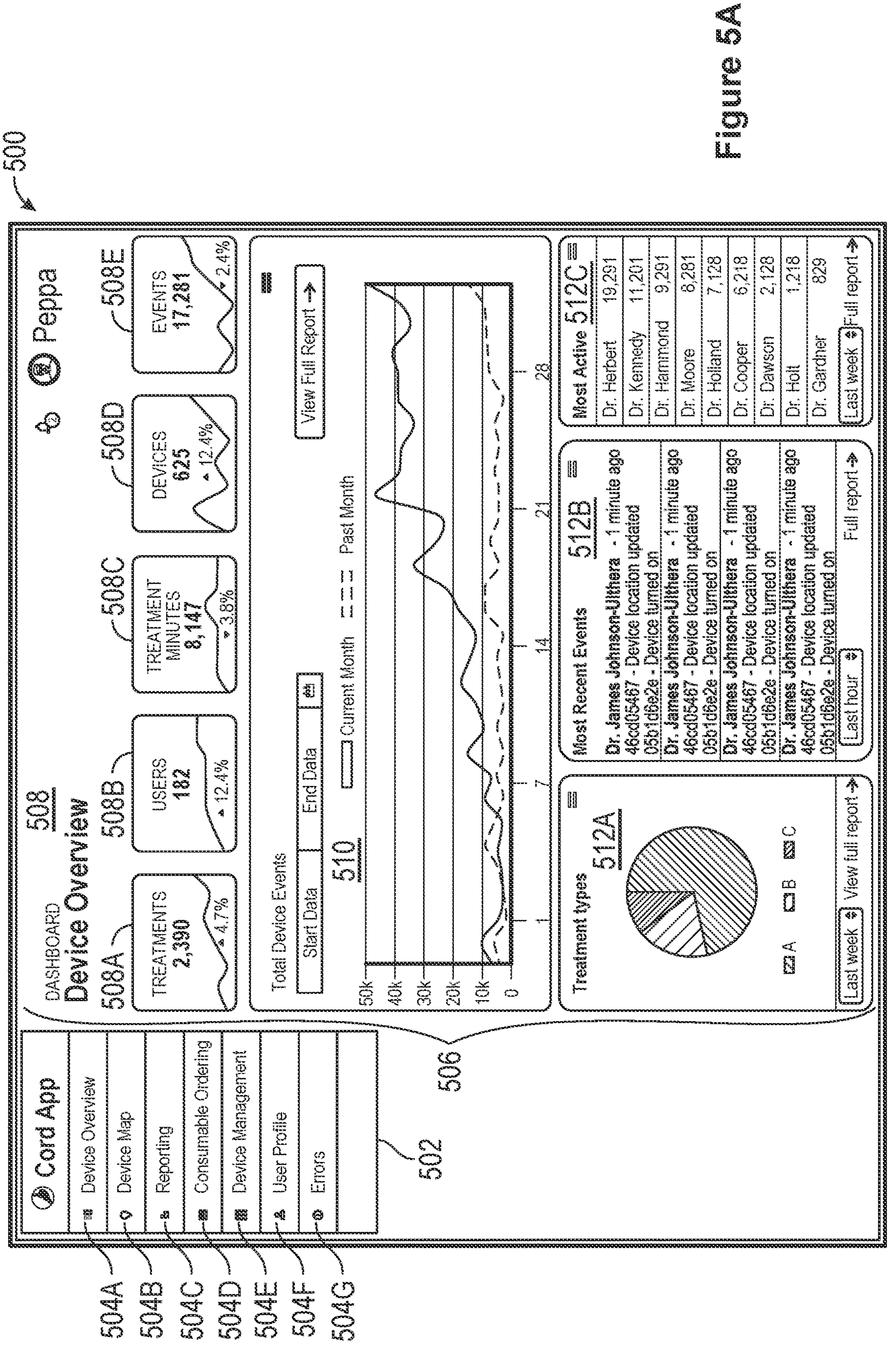
FIGS. 5A-5C are three example user interfaces that are presented to a user, in accordance with some embodiments.
Figure 5B:
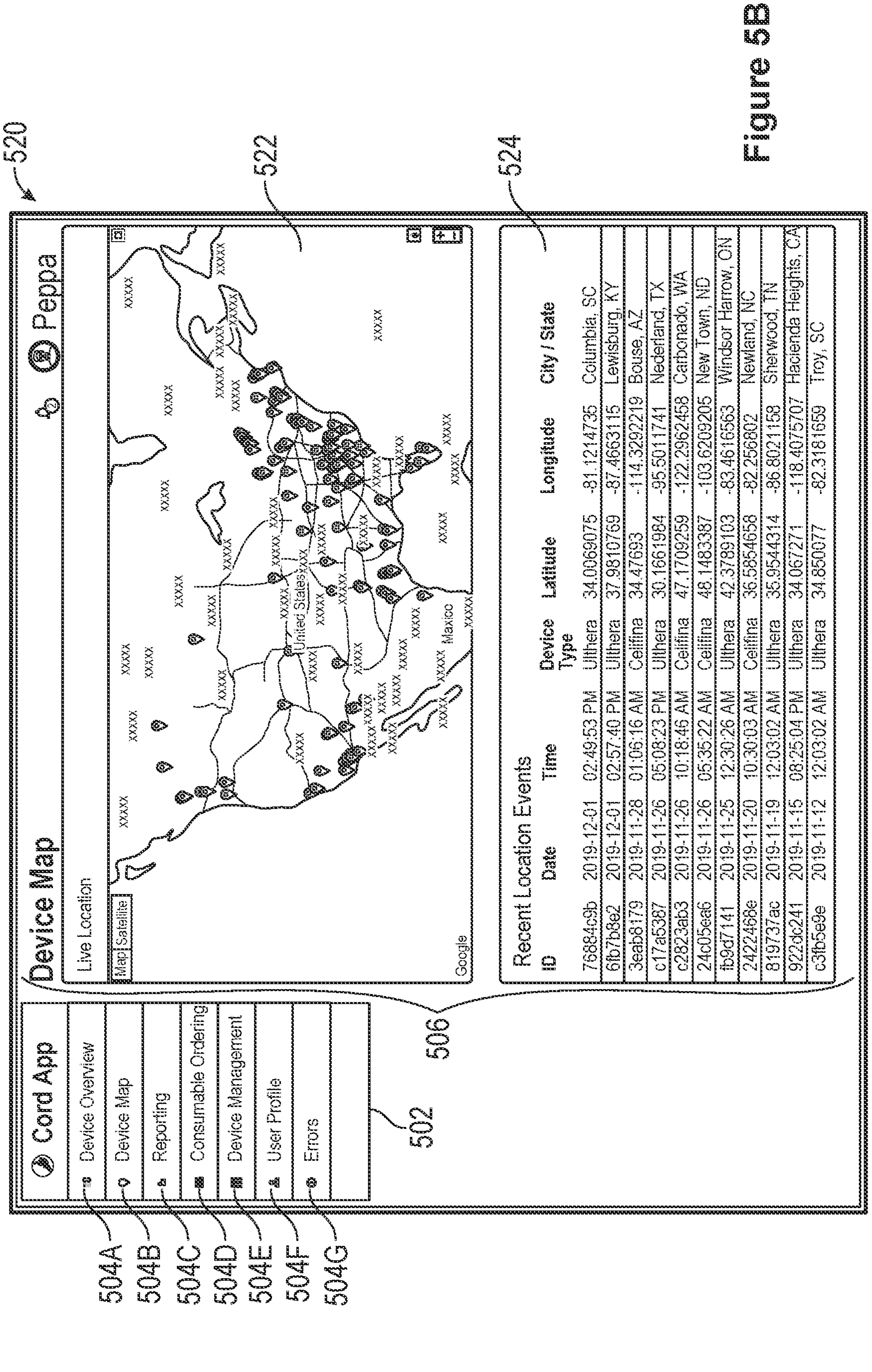
Figure 5C:
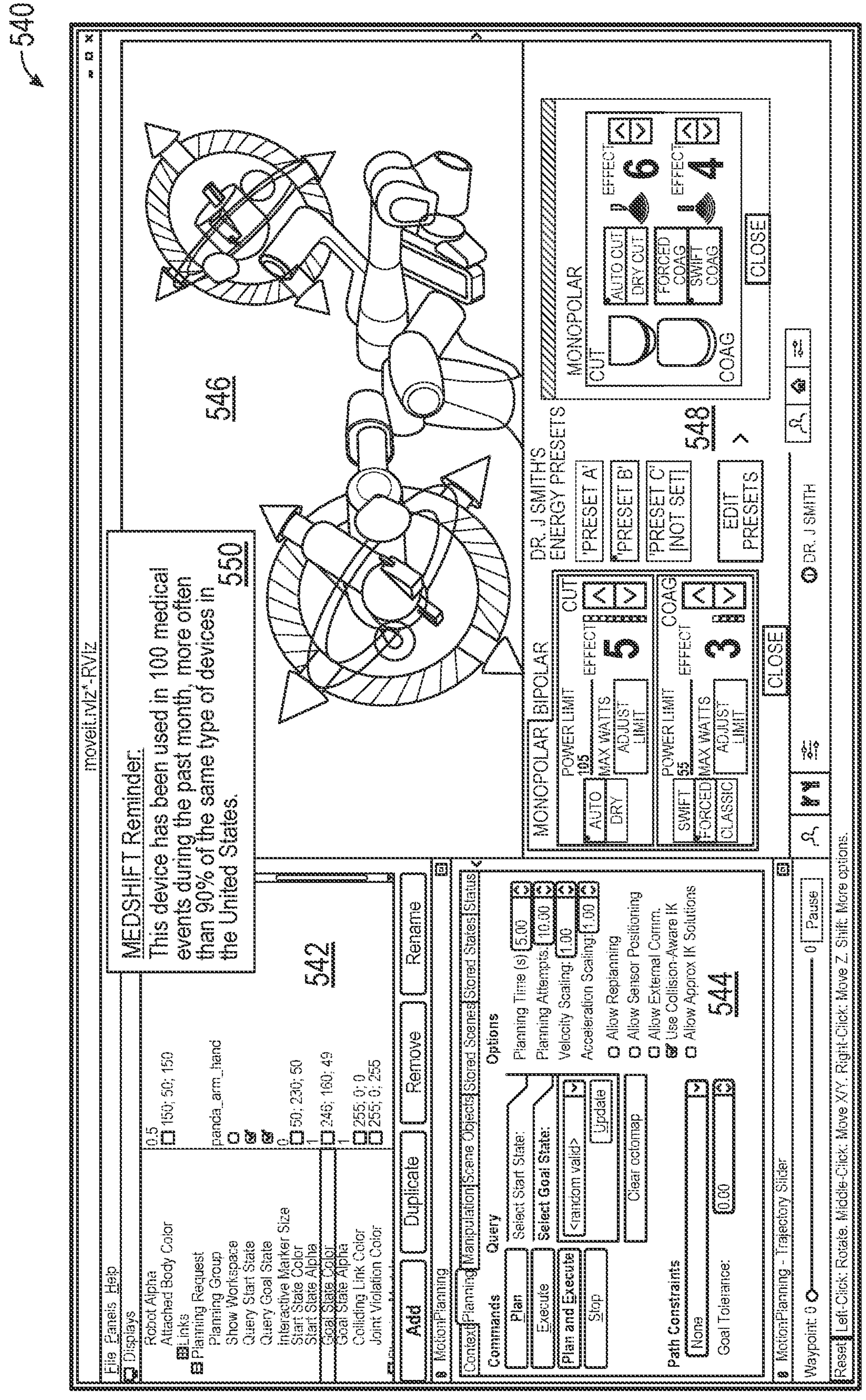

FIGS. 5A, 5B, and 5C are three example user interfaces 500, 520, and 540, which are presented to a user, in accordance with some embodiments. A message 130 generated by a power cord sever 108 is displayed as part of each of the user interfaces 500, 520, and 540. The message 130 may include an alert, a notification, a report, or an instruction concerning a medical procedure. Referring to FIGS. 5A and 5B, the user interface 500 or 520 is loaded in a power cord application (e.g., the application 634 in FIG. 6A or 6B) executed by an electronic device (e.g., a client device 112 or a medical device 102). The power cord application is configured to facilitate monitoring medical procedures that are implemented by medical devices 102 distributed in different medical facilities based on power profiles 120 of these medical procedures. The power cord application may be a browser-based application or a dedicated data application. Each of the user interfaces 500 and 520 of the power cord application includes a menu region 502 having a plurality of affordances 504 and an information display region 506. Each affordance 504 corresponds to different content displayed on the information display region 506. In response to selection of one of the plurality of affordances 504, the power cord application displays corresponding different content on the information display region 506. For a subset of the affordances 504, the corresponding different content corresponds to the message 130 determined based on the collected power profiles 120. Part or all of the message 130 is displayed in the user interface 500 and 520 of the power cord application executed by the electronic device.

The plurality of affordances 504 includes one of more of: a device overview affordance 504A, a device map affordance 504B, a reporting affordance 504C, a consumable ordering affordance 504D, a device management affordance 504E, a user profile affordance 504F, and an error affordance 504G. In response to selection of the device overview affordance 504A, the user interface 500 is displayed with the information display region 506 as shown in FIG. 5A. Content displayed in the information display region 506 includes a device overview 508 of medical procedures that satisfy predefined criteria (e.g., including time and location limitations). The device overview 508 may include one or more of: the total number of medical procedures (i.e., treatments) 508A, the number of users of power data 508B, the total treatment time of these medical procedures 508C, the number of medical devices 508D, and the number of device events 508E. In some situations, a plot 510 is generated to provide more information for a subset of the device overview 508 (e.g., the number of device events 508E). In this example, the plot 510 shows a fluctuation of the number of device events 508E over the current month and the past month. In some embodiments, additional content 512 is displayed to provide insight into the power profiles 120 collected by the power cord server 108. For example, the additional content 512 includes a summary of treatment types 512A, a record of most recent events 512B, and/or a list of the most active doctors 512C.

Among content displayed in the information display region 506, at least the total treatment time of these medical procedures 508C is associated with numeric operational parameters 436 of the medical procedures monitored by the power cord server 108. In some embodiments, in response to user selection of another item in the device overview 508, the user interface 500 is refreshed to display additional information (e.g., one or more numeric operational parameters 436 received with the message 130) on the information display region 506. In some embodiments, the message 130 may include numeric operational parameters 436 of each medical procedure while none of the parameters 436 is displayed for each individual procedure or in an aggregated context. Rather, the information display region 506 may be focused on displaying a statistical summary of the medical procedures collected based on the predefined criteria (e.g., displaying the total number of medical procedures 508A and the number of device events 508E).

Referring to FIG. 5B, in response to selection of the device map affordance 504B, the user interface 520 is displayed as shown in FIG. 5B. The information display region 506 displays a map 522 showing distribution of medical devices 102 from which power profiles 120 of medical procedures have been collected, and a list 524 of recent location events. Each event in the list 524 is described with a device identification, an event date, an event time, a device type, and location information. Content displayed in the information display region 506 of the user interface 520 may include the numeric operational parameters 436 of the associated medical procedures. In some embodiments not shown in FIG. 5B, the information display region 506 of the user interface 520 includes a subset of the numeric operational parameters 436 of the associated medical procedures. For example, in response to a selection of one of the recent location events in the list 524, the user interface 520 is refreshed to display details of the selected recent location event including one or more numeric operational parameters 436 of a medical procedure associated with the selected recent location event.

Referring to FIG. 5C, the user interface 540 is loaded in a medical device application (e.g., the application 630 in FIG. 6A or 6B) executed by an electronic device (e.g., a medical device 102). The medical device application may be executed offline or jointly with a medical device server 114. A primary function of the medical device application is to facilitate implementations of medical procedures (e.g., before, during, or after the procedures). In this example, the user interface 540 includes a first region 542 for displaying key medical parameters, a second region 544 for adjusting treatment settings, a third region 546 for visually showing a medical tool, and a fourth region 548 for adjusting some key settings directly. The medical device application includes a power cord plug-in program (e.g., the program 632 in FIG. 6A or 6B) executed jointly with the power cord server 108, which is distinct from the medical device server 114 associated with the medical device application. The power cord plug-in program is configured to display part or all of the message 130 received from the power cord server 108 on the user interface 540 of the medical device application. In some embodiments, the message 130 is displayed in a dedicated region of the user interface 540, such as in a fixed region of the medical device application. Alternatively, in some embodiments as shown in FIG. 5C, the message 130 is displayed in a pop-out window 550 of the user interface 540, which is overlaid on any of the regions 542-548, and disappears after a predefined duration of time or in response to a user action. In this example, the message 130 is a notification: "This device has been used in 100 medical events during the past month, more often than 90% of the same type of devices in the United States".

In some embodiments, the medical device 102 displaying any of the user interfaces 500, 520, or 540 uses the power cord device 106 to power its medical procedures and report its own power profiles 120, while subscribing to data service provided by the power cord server 108. Conversely, in some embodiments, the medical device 102 displaying any of the user interfaces 500, 520, or 540 subscribes to data service provided by the power cord server 108 only. However, it does not use the power cord device 106 to power its medical procedures or report its own power profiles 120. Additionally, in some embodiments not shown, a medical device 102 does not subscribe to data service provided by the power cord server 108, while still using the power cord device 106 to power its medical procedures or report its own power profiles 120. Optionally, the power cord server 108 is configured to separately use the power cord device 106 and subscription to the data service. In some embodiments, the power cord server 108 is configured to associate use of the power cord device 106 and subscription to the data service, thereby providing the data service to users of the power cord devices 106 automatically. The power cord server 108 can further extend the data service to other subscribers that do not use the power cord devices 106.

Figure 6A:
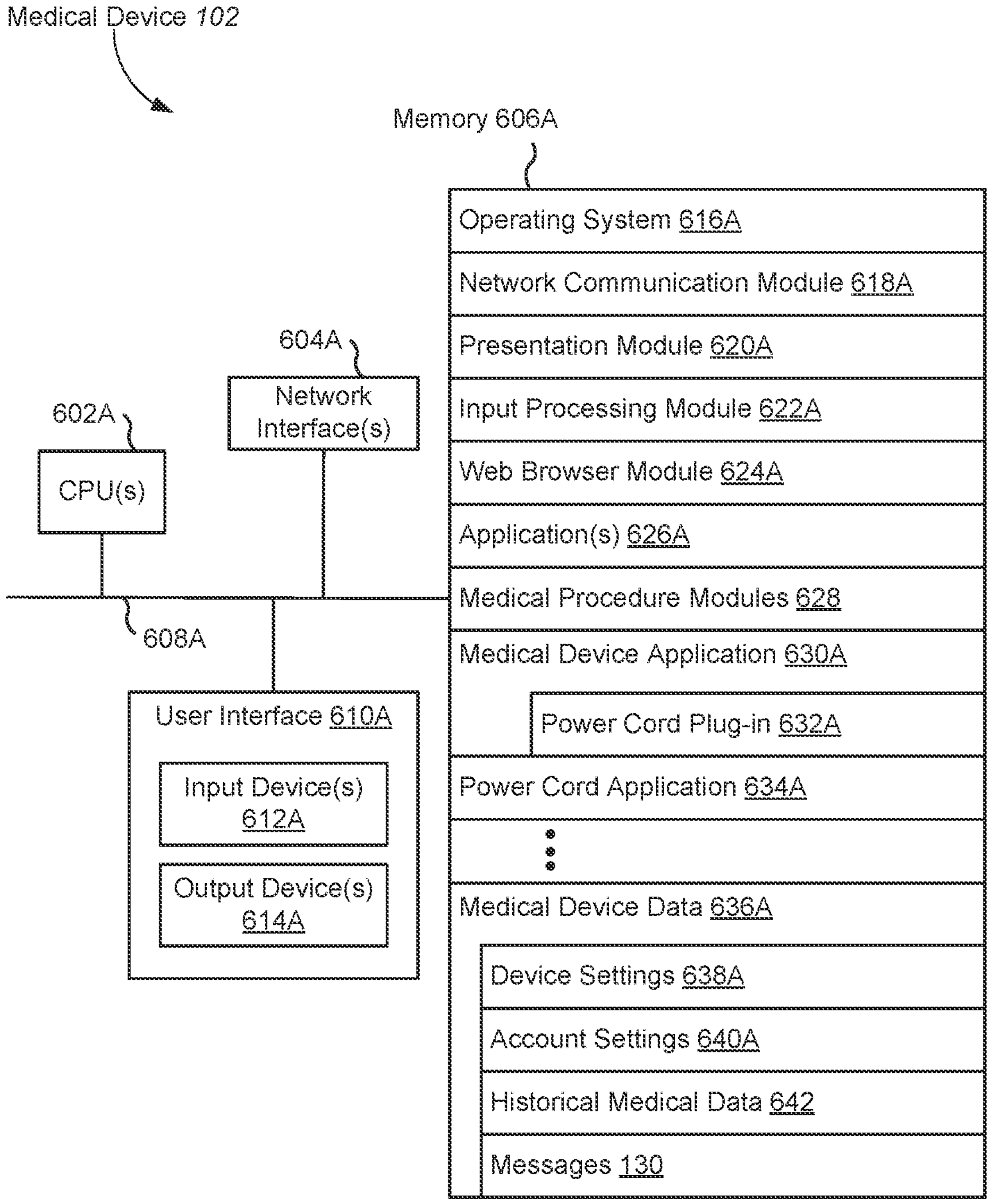
FIG. 6A is a block diagram of an example medical device for implementing medical procedures, in accordance with some embodiments.

FIG. 6A is a block diagram of an example medical device 102 for performing medical procedures, in accordance with some embodiments. The medical device 102 typically includes one or more processing units (CPUs) 602A, one or more network interfaces 604A, memory 606A, and one or more communication buses 608A for interconnecting these components (sometimes called a chipset). The medical device 102 includes one or more user interface devices 610A. The user interface devices 610A include one or more input devices 612A, which facilitate user input, such as a keyboard, a mouse, a voice-command input unit or microphone, a touch screen display, a touch-sensitive input pad, a gesture capturing camera, or other input buttons or controls. Furthermore, in some embodiments, the medical device 102 uses a microphone and voice recognition or a camera and gesture recognition to supplement or replace the keyboard. In some embodiments, the one or more input devices 612A include one or more cameras, scanners, or photo sensor units for capturing images, for example, of graphic serial codes printed on electronic devices. The medical device 102 also includes one or more output devices 614A, which enable presentation of user interfaces (e.g., the interfaces 500, 520, and 540 in FIGS. 5A-5C) and display content, including one or more speakers and/or one or more visual displays. The user interface device 610A further include some transducer portions for implementing medical procedures. For example, if the medical device 102 is a medical imaging device, the input devices 612A of the medical device 102 includes a medical sensor configured to collect medical information during the medical procedure.

The memory 606A includes high-speed random access memory, such as DRAM, SRAM, DDR RAM, or other random access solid state memory devices. In some embodiments, the memory includes non-volatile memory, such as one or more magnetic disk storage devices, one or more optical disk storage devices, one or more flash memory devices, or one or more other non-volatile solid state storage devices. In some embodiments, the memory 606A includes one or more storage devices remotely located from one or more processing units 602A. The memory 606A, or alternatively the non-volatile the memory within the memory 606A, includes a non-transitory computer readable storage medium. In some embodiments, the memory 606A, or the non-transitory computer readable storage medium of memory 606A, stores the following programs, modules, and data structures, or a subset or superset thereof:

- an operating system 616A, which includes procedures for handling various basic system services and for performing hardware dependent tasks;
- a network communication module 618A, which connects each medical device 102 to other devices (e.g., medical device server 114, power cord server 108, client device 112) via one or more network interfaces 604A (wired or wireless) and one or more communication networks 110, such as the Internet, other wide area networks, local area networks, metropolitan area networks, and so on;
- a presentation module 620A, which enables presentation of information (e.g., a graphical user interface for application 626A, widgets, websites and web pages thereof, and/or games, audio, and/or video content) at each medical device 102 via one or more output devices 614A (e.g., displays or speakers);
- an input processing module 622A, which detects one or more user inputs or interactions from one of the one or more input devices 612A and interprets the detected input or interaction;
- a web browser module 624A, which navigates, requests (e.g., via HTTP), and displays websites and web pages thereof, including a web interface for logging into a user account associated with the medical device 102 or another electronic device. The web browser module 624A also controls the medical or electronic device if it is associated with the user account, and edits and reviews settings and data that are associated with the user account;
- one or more user applications 626A, which execute at the medical device 102;
- a medical procedure module 628A, which performs medical procedures of the medical device 102;
- a medical device application 630A, which performs medical procedures via the medical procedure module 628A. The medical device application 630A includes a power cord plug-in program 632A to receive and present information concerning power usage of different medical devices distributed across different medical facilities within the medical device application 630A;
- a power cord application 634A dedicated to receiving from a power cord server 108 information concerning power usage of different medical devices distributed across different medical facilities and presenting such information within the power cord application 634A;
- medical device data 636A, including:
  - device settings 638A, including common device settings (e.g., service tier, device model, storage capacity, processing capabilities, communication capabilities, and/or medical procedure settings) of the medical device 102;
  - user account information 640A for the one or more user applications 626A, medical device application 630A, and power cord application 634A (e.g., user names, security questions, account history data, user preferences, and predefined account settings);
  - historical medical data 642 associated with the medical procedures previously implemented by the medical device 102; and
  - messages 130, which specify the medical procedures and corresponding numeric operational parameters 436. The messages 130 are generated and provided by the power cord server 108 based on power profiles 120 collected from different medical devices 102, which may include or not include the medical device 102 itself.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, modules or data structures, and thus various subsets of these modules may be combined or otherwise re-arranged in various embodiments. In some embodiments, the memory 606A stores a subset of the modules and data structures identified above. In some embodiments, the memory 606A stores additional modules and data structures not described above.

Figure 6B:
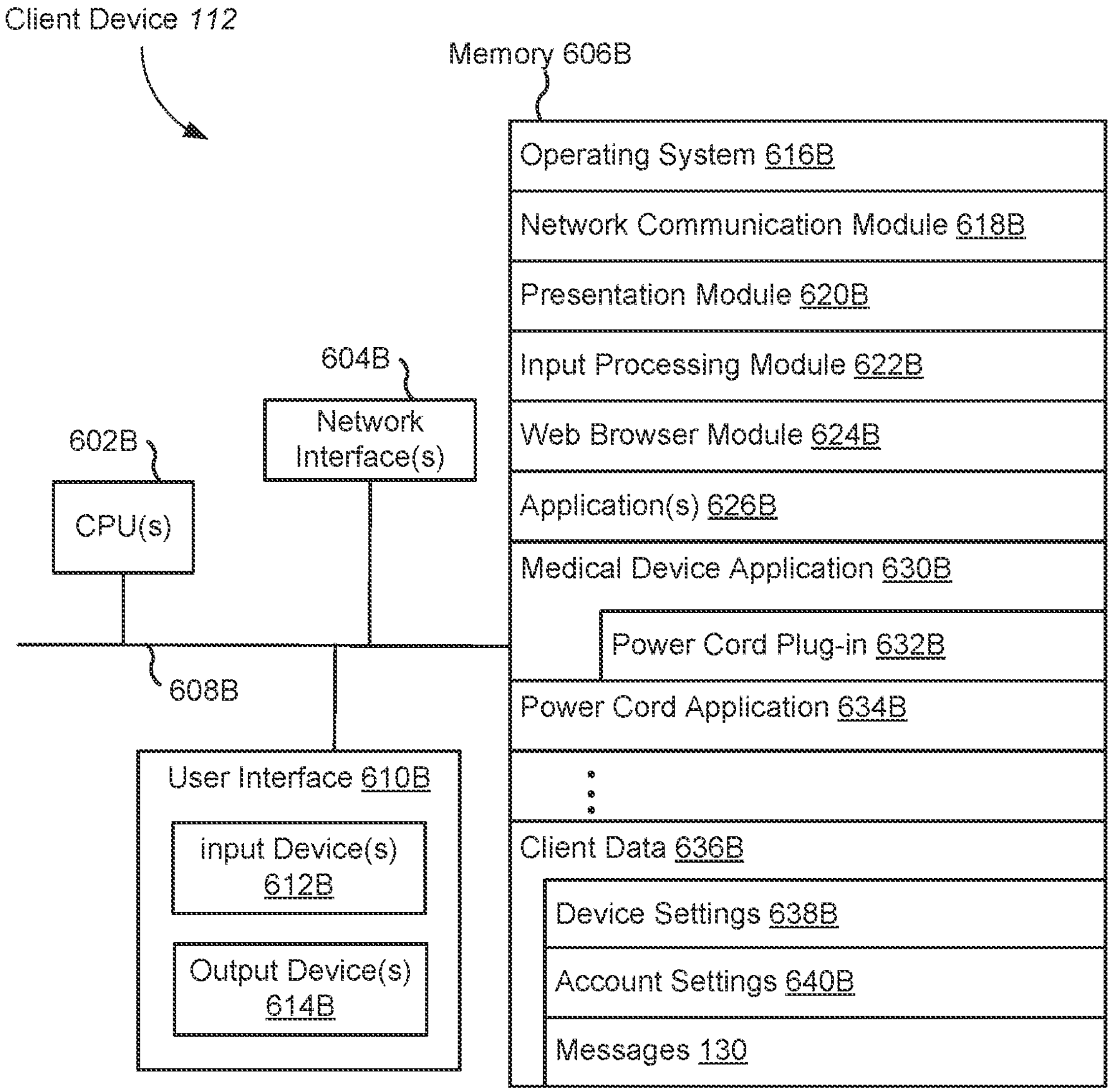
FIG. 6B is a block diagram of an example client device for presenting information of medical procedures implemented at distinct medical devices, in accordance with some embodiments.

FIG. 6B is a block diagram of an example client device 112 for presenting information of medical procedures implemented at distinct medical devices 102, in accordance with some embodiments. Examples of the client device 112 include, but are not limited to, a desktop computer, a laptop computer, a tablet computer, and a mobile phone. The client device 112 typically includes one or more processing units (CPUs) 602B, one or more network interfaces 604B, memory 606B, and one or more communication buses 608B for interconnecting these components (sometimes called a chipset). The client device 112 includes one or more user interface devices 610B. The user interface devices 610B include one or more input devices 612B, which facilitate user input, such as a keyboard, a mouse, a voice-command input unit or microphone, a touch screen display, a touch-sensitive input pad, a gesture capturing camera, or other input buttons or controls. Furthermore, in some embodiments, the medical device 102 uses a microphone and voice recognition or a camera and gesture recognition to supplement or replace the keyboard. In some embodiments, the one or more input devices 612B include one or more cameras, scanners, or photo sensor units for capturing images, for example, of graphic serial codes printed on electronic devices. The client device 112 also includes one or more output devices 614B, which enable presentation of user interfaces (e.g., the interfaces 500, 520, and 540 in FIGS. 5A-5C) and display content, including one or more speakers and/or one or more visual displays.

The memory 606B includes high-speed random access memory, such as DRAM, SRAM, DDR RAM, or other random access solid state memory devices. In some embodiments, the memory includes non-volatile memory, such as one or more magnetic disk storage devices, one or more optical disk storage devices, one or more flash memory devices, or one or more other non-volatile solid state storage devices. In some embodiments, the memory 606B includes one or more storage devices remotely located from one or more processing units 602B. The memory 606B, or alternatively the non-volatile memory within the memory 606B, includes a non-transitory computer readable storage medium. In some embodiments, the memory 606B, or the non-transitory computer readable storage medium of the memory 606B, stores the following programs, modules, and data structures, or a subset or superset thereof:

- an operating system 616B, which includes procedures for handling various basic system services and for performing hardware dependent tasks;
- a network communication module 618B, which connects each client device 112 to other devices (e.g., the power cord server 108, the medical device server 114, and or the client device 112) via one or more network interfaces 604B (wired or wireless) and one or more communication networks 110, such as the Internet, other wide area networks, local area networks, metropolitan area networks, and so on;
- a presentation module 620B, which enables presentation of information (e.g., a graphical user interface for the application 626B, widgets, websites and web pages thereof, and/or games, audio, and/or video content) at each client device 112 via one or more output devices 614B (e.g., displays or speakers);
- an input processing module 622B, which detects one or more user inputs or interactions from one of the one or more input devices 612B and interprets the detected input or interaction;
- a web browser module 624B, which navigates, requests (e.g., via HTTP), and displays websites and web pages thereof, including a web interface for logging into a user account associated with the client device 112 or another medical or client device. The web browser module 624B also controls the medical or client device if it is associated with the user account, and edits and reviews settings and data that are associated with the user account;
- one or more user applications 626B, which executes by the client device 112 (e.g., games, social network applications, smart home applications, and/or other web or non-web based applications for controlling another medical or client device and reviewing data captured by such devices);
- a medical device application 630B, which controls medical procedures performed by a medical device 102 remotely. The medical device application 630B includes a power cord plug-in program 632B for receiving and presenting information concerning power usage of different medical devices distributed across different medical facilities within the medical device application 630B;
- a power cord application 634B dedicated to receiving from a power cord server 108 information concerning power usage of different medical devices distributed across different medical facilities and presenting such information within the power cord application 634B;
- client data 636B, including:
  - device settings 638B, including common device settings (e.g., service tier, device model, storage capacity, processing capabilities, communication capabilities, and/or medical procedure settings) of the client device 112;
  - user account information 640B for the one or more user applications 626B, medical device application 630B, and power cord application 634B (e.g., user names, security questions, account history data, user preferences, and predefined account settings); and
  - messages 130, which specify the medical procedures and corresponding numeric operational parameters 436. The messages are generated and provided by the power cord server 108 based on power profiles 120 collected from different medical devices 102.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, modules, or data structures, and thus various subsets of these modules may be combined or otherwise re-arranged in various embodiments. In some embodiments, the memory 606B stores a subset of the modules and data structures identified above. In some embodiments, the memory 606B stores additional modules and data structures not described above.

Figure 6C:
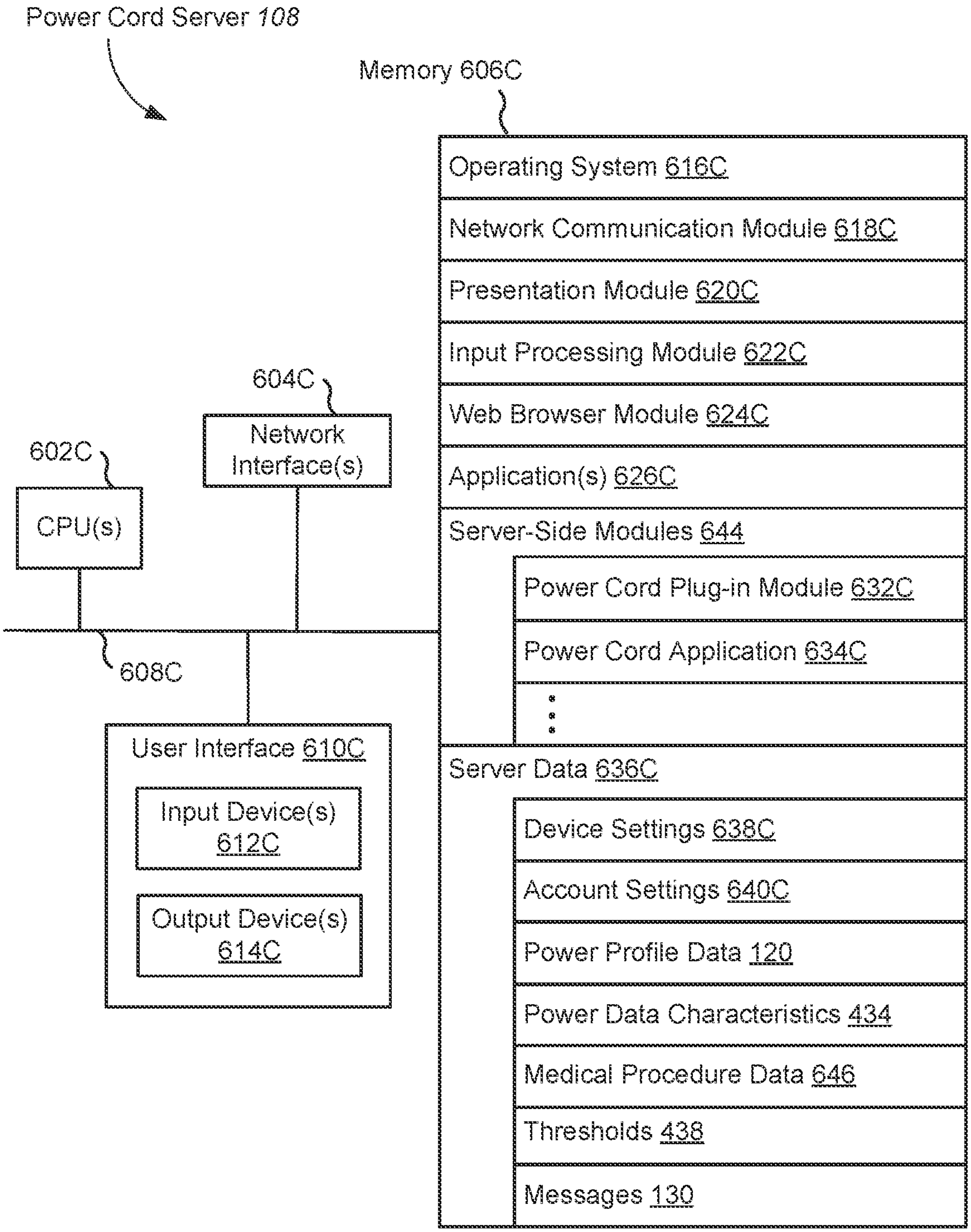
FIG. 6C is a block diagram of a power cord server 108 for collecting power profiles and providing information of medical procedures to users, in accordance with some embodiments.
Figure 7A:
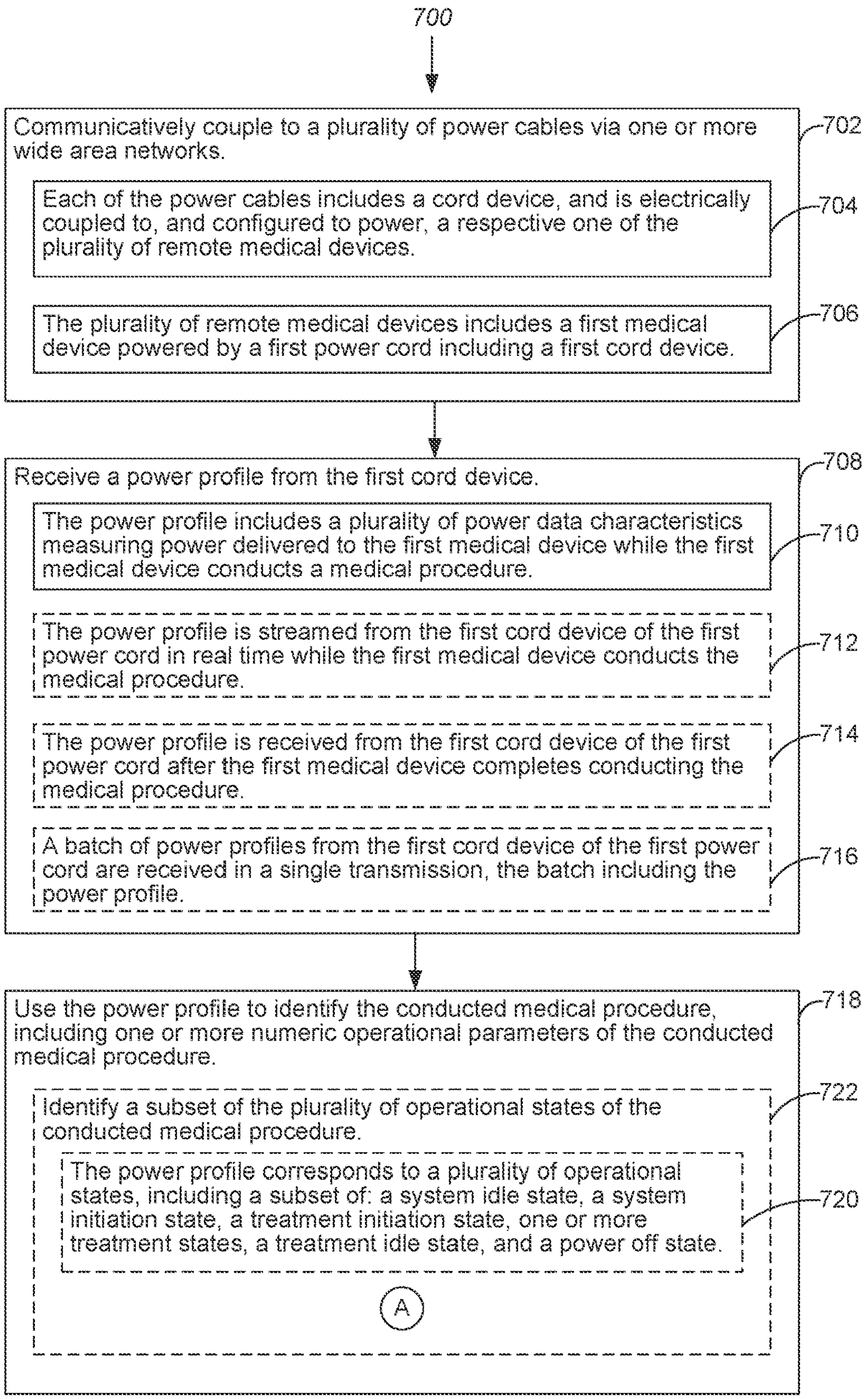
FIGS. 7A-7D provide a flow diagram of a data management method implemented at a power cord server, in accordance with some embodiments.
Figure 7B:
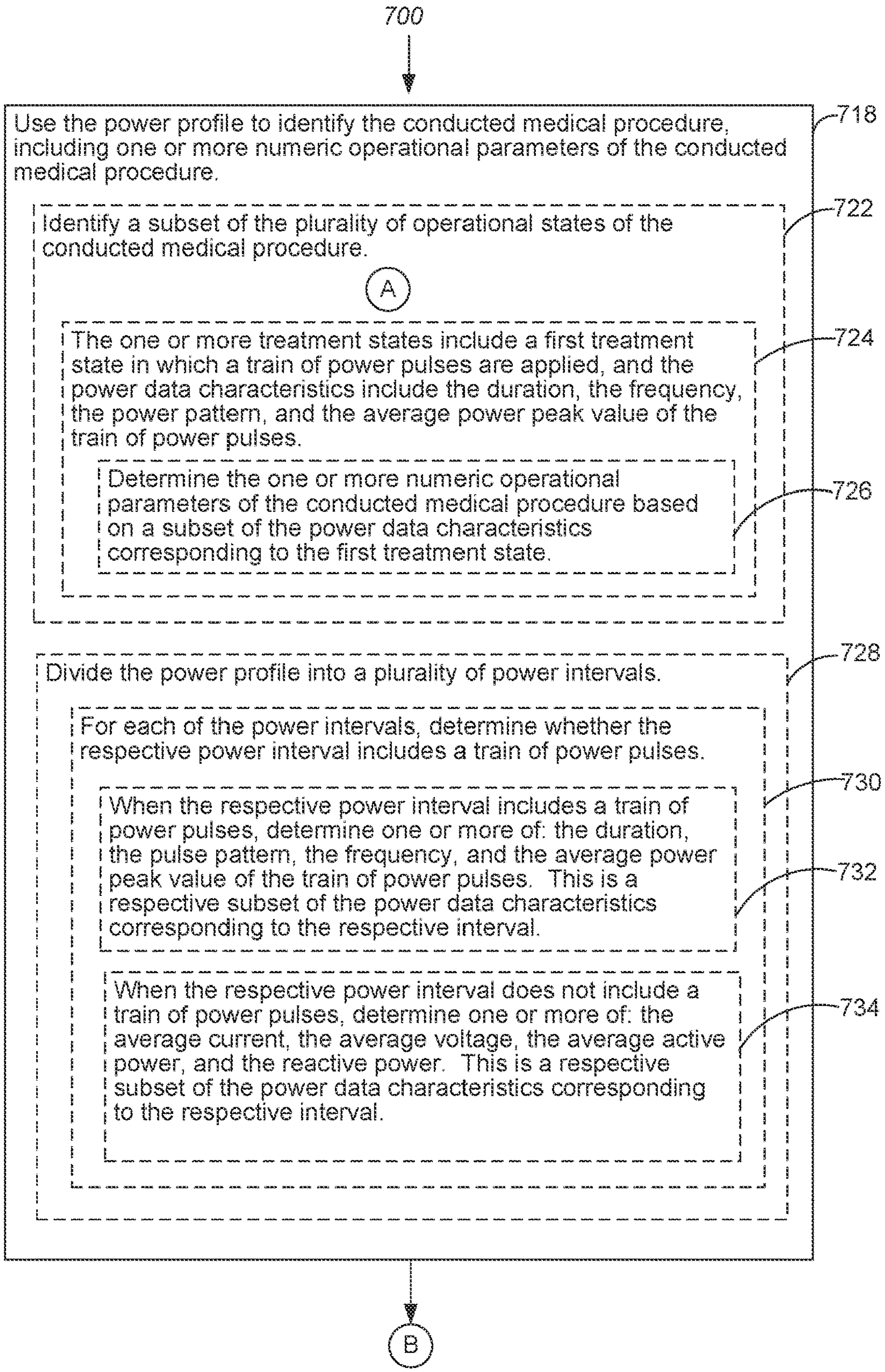
Figure 7C:
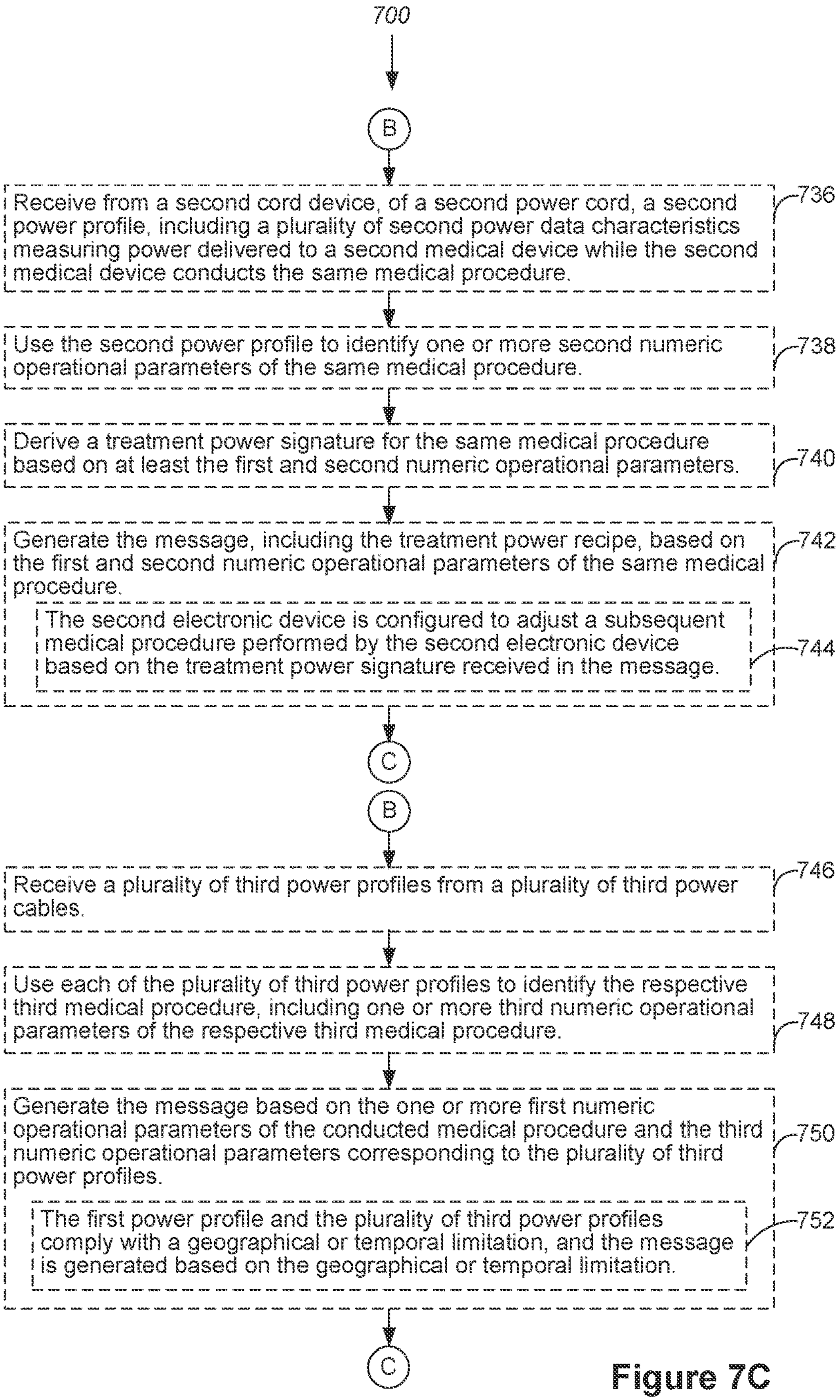
Figure 7D:
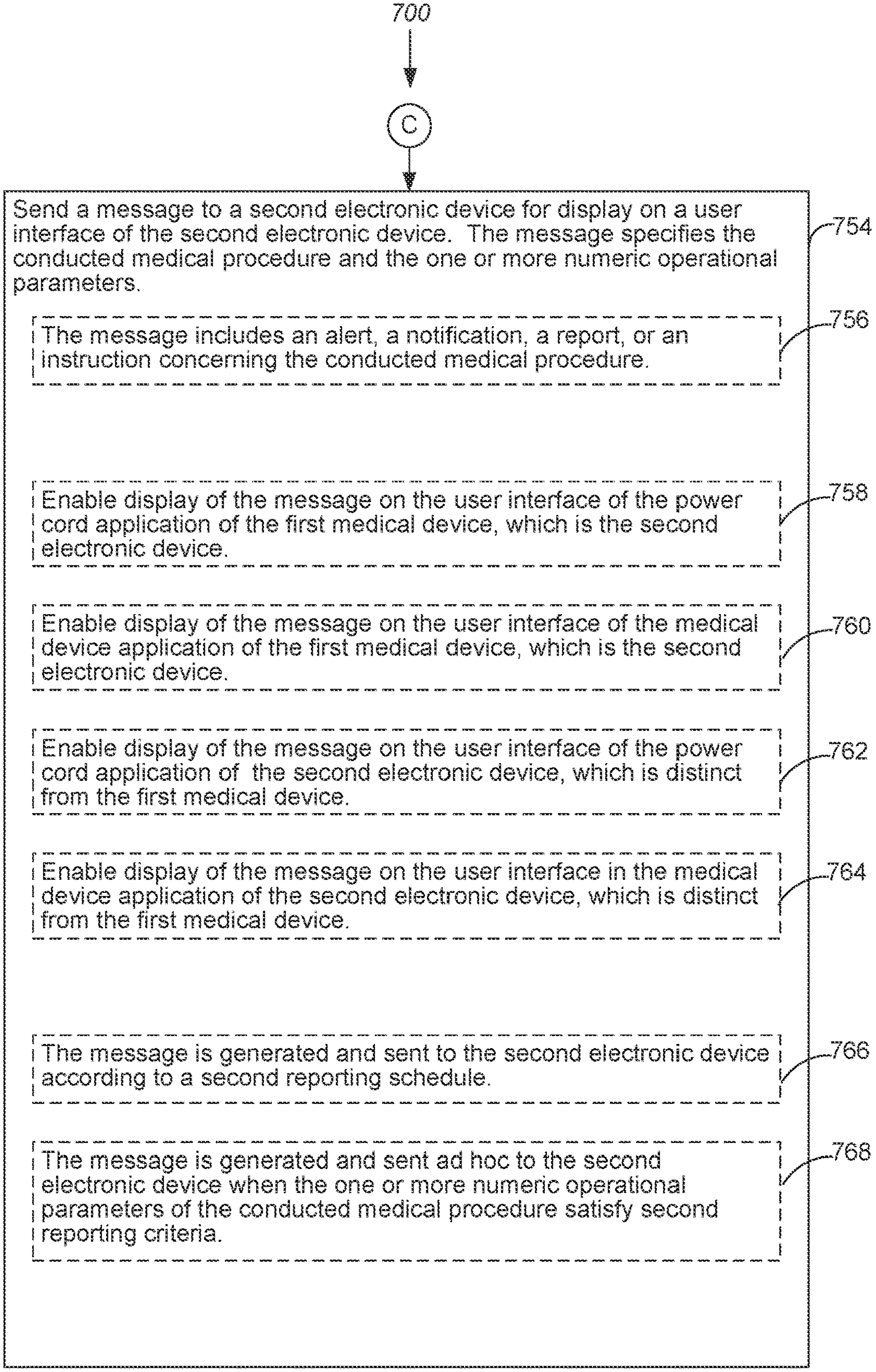

FIG. 6C is a block diagram of a power cord server 108 for collecting power profiles 120 and providing information of medical procedures to users, in accordance with some embodiments. Examples of the power cord server 108 include, but are not limited to, a desktop computer, a laptop computer, a tablet computer, or a mobile phone. The power cord server 108 typically includes one or more processing units (CPUs) 602C, one or more network interfaces 604C, memory 606C, and one or more communication buses 608C for interconnecting these components (sometimes called a chipset). The power cord server 108 includes one or more user interface devices 610C. The user interface devices 610C include one or more input devices 612C, which facilitate user input, such as a keyboard, a mouse, a voice-command input unit or microphone, a touch screen display, a touch-sensitive input pad, a gesture capturing camera, or other input buttons or controls. Furthermore, in some embodiments, the medical device 102 uses a microphone and voice recognition or a camera and gesture recognition to supplement or replace the keyboard. In some embodiments, the one or more input devices 612C include one or more cameras, scanners, or photo sensor units for capturing images, for example, of graphic serial codes printed on electronic devices. The power cord server 108 also includes one or more output devices 614C, which enable presentation of user interfaces and display content, including one or more speakers and/or one or more visual displays.

The memory 606C includes high-speed random access memory, such as DRAM, SRAM, DDR RAM, or other random access solid state memory devices. In some embodiments, the memory includes non-volatile memory, such as one or more magnetic disk storage devices, one or more optical disk storage devices, one or more flash memory devices, or one or more other non-volatile solid state storage devices. In some embodiments, the memory 606C includes one or more storage devices remotely located from one or more processing units 602C. The memory 606C, or alternatively the non-volatile memory within memory 606C, includes a non-transitory computer readable storage medium. In some embodiments, the memory 606C, or the non-transitory computer readable storage medium of the memory 606C, stores the following programs, modules, and data structures, or a subset or superset thereof:

- an operating system 616C, which includes procedures for handling various basic system services and for performing hardware dependent tasks;
- a network communication module 618C, which connects the power cord server 108 to other devices (e.g., power cord devices 106, medical devices 102, and/or client devices 112) via one or more network interfaces 604C (wired or wireless) and one or more communication networks 110, such as the Internet, other wide area networks, local area networks, metropolitan area networks, and so on;
- a presentation module 620C, which enables presentation of information (e.g., a graphical user interface for the application 626C, widgets, websites and web pages thereof, audio and/or video content) at the power cord server 108 via one or more output devices 614C (e.g., displays or speakers);
- an input processing module 622C, which detects one or more user inputs or interactions from one of the one or more input devices 612C and interprets the detected input or interaction;
- a web browser module 624C, which navigates, requests (e.g., via HTTP), and displays websites and web pages thereof, including a web interface for logging into a user account associated with the power cord server 108, controls predefined criteria (e.g., including time and location limitations) of power cord devices 106 if associated with the user account, and edits and reviews settings and data that are associated with the user account;
- one or more user applications 626C, which execute by the power cord server 108 (e.g., web or non-web based applications for controlling predefined criteria, such as time and location limitations, of power cord devices 106 and reviewing data captured by such power cord devices 106);
- server-side modules 644, including (1) a power cord plug-in module 632C, enabling display in a medical device application 630 of information concerning power usage of different medical devices 102 that are distributed across different medical facilities and/or (2) a power cord application 634C dedicated to sending to a client-side power cord application 634A or 634B information concerning power usage of different medical devices 102 and presenting such information in the client-side power cord application 634A or 634B;
- server data 636C, including:
  - device settings 638C, which include common device settings (e.g., service tier, device model, storage capacity, processing capabilities, communication capabilities, and/or medical procedure settings) of the power cord server 108;
  - user account information 640C for the one or more user applications 626C, the power cord plug-in module 632C, and the power cord application 634C (e.g., user names, security questions, account history data, user preferences, and predefined account settings);
  - power profile data 120 collected from different medical devices 102;
  - power data characteristics 434 extracted from the power profile data 120 in association with modes or operational states of the medical device 102;
  - medical procedure data 646, which is determined based on the power data characteristics 434, including, but not limited to, the device type of the medical device 102, one of the operational mode 420 or the idle mode 418, operational states 422-432, the type of each medical procedure, and numeric operational parameters 436 of each medical procedure;
  - power thresholds 438 for deriving the medical procedure data 646 from the power data characteristics 434 that are extracted from the power profiles 120; and
  - messages 130, which specify the medical procedures and corresponding numeric operational parameters 436.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, modules or data structures, and thus various subsets of these modules may be combined or otherwise re-arranged in various embodiments. In some embodiments, the memory 606C stores a subset of the modules and data structures identified above. In some embodiments, the memory 606C stores additional modules and data structures not described above.

FIGS. 7A-7D provide a flow diagram of a data management method 700 implemented at a power cord server 108, in accordance with some embodiments. In some embodiments, the method 700 is governed by instructions that are stored in a non-transitory computer readable storage medium and are executed by one or more processors of the power cord server 108. Each of the operations shown in FIGS. 7A-7D may correspond to instructions stored in the computer memory or computer readable storage medium (e.g., the memory 606C in FIG. 6C) of the power cord server 108. The computer readable storage medium may include a magnetic or optical disk storage device, solid state storage devices such as Flash memory, or other non-volatile memory device or devices. The computer readable instructions stored on the computer readable storage medium may include one or more of: source code, assembly language code, object code, or other instruction format that is interpreted by one or more processors. Some operations in the method 700 may be combined and/or the order of some operations may be changed. In some embodiments, the method 700 is governed by instructions stored in a server-side module 644 for a power cord plug-in module 632B or a power cord application 634B.

The power cord server 108 hosts a centralized power data management system for a plurality of remote medical devices 102 located at one or more medical facilities. In this centralized power data management system, the power cord sever 108 is communicatively coupled (702) to a plurality of power cables 104 via one or more wide area networks (WANs) 110. Each of the power cables 104 includes (704) a power cord device 106, and is electrically coupled to, and configured to power, a respective one of the plurality of remote medical devices 102. The plurality of remote medical devices 102 includes (706) a first medical device 102A powered by a first power cable 104A including a first cord device 106A. In some embodiments, the one or more WANs 110 include a cellular network, and the plurality of power cables 104 are communicatively coupled to the power cord server 108 via the cellular network without accessing any local network device or local area network. In some embodiments, communication via the cellular network is private and encrypted.

The power cord server 108 receives (708) a power profile 120 from the first cord device 106A. The power profile 120 includes (710) a plurality of power data characteristics 434 measuring power delivered to the first medical device 102A while the first medical device 102A conducts a medical procedure. In some embodiments, the power profile 120 is streamed (712) from the first cord device 106A of the first power cable 104A in real time while the first medical device 102A conducts the medical procedure. Alternatively, in some embodiments, the power profile 120 is received (714) from the first cord device 106A of the first power cable 104A after the first medical device 102A completes conducting the medical procedure. Additionally and alternatively, a batch of power profiles from the first cord device 106A of the first power cable 104A are received (716) in a single transmission according to a first reporting schedule (e.g., every day or every week). The batch includes the power profile 120 together with one or more additional power profiles 120 of one or more additional medical procedures, and each of the additional procedures was previously conducted at the first medical device 102A. In some embodiments, the power profile 120 is sent to the power cord server 108 in accordance with a determination that the power profile 120 of the medical procedure satisfies certain predefined reporting criteria (e.g., the average active power 406 reaching a predefined threshold or a predefined number of pulses being detected in the active power 406).

After receiving the power profile 120, the power cord server 108 uses (718) the power profile 120 to identify the conducted medical procedure, including one or more numeric operational parameters 436 of the conducted medical procedure. In some embodiments, the power profile corresponds (720) to a plurality of operational states 422-432, including a subset of: a system idle state 424, a system initiation state 422, a treatment initiation state 426, one or more treatment states 428, a treatment idle state 430, and a power off state 432. The power cord server 108 identifies (722) a subset of the plurality of operational states 422-432 of the conducted medical procedure. Further, in some embodiments, the one or more treatment states 428 include (724) a first treatment state 428A in which a train of power pulses 450A are applied, and the plurality of power data characteristics 434 includes the duration, the frequency, the power pattern, and the average power peak value of the train of power pulses 450A. The power cord server 108 determines (726) the one or more numeric operational parameters 436 of the conducted medical procedure based on a subset of the power data characteristics 434 corresponding to the first treatment state 428A. Additionally, in some embodiments, each of the plurality of operational states 422-432 is defined according to at least one power threshold 438 associated with a respective subset of the power data characteristics 434. The power cord server 108 determines and adjusts the at least one power threshold 438 associated with each of the plurality of operational states 422-432 based on a deep learning technique. Additionally, in some embodiments, each of the plurality of operational states 422-432 is recognized or classified from the power profiles 120 using a deep learning technique.

Referring to FIG. 4A, in some embodiments, the power cord server 108 divides (728) the power profile 120 into a plurality of power intervals. For each of the power intervals, the power cord server 108 determines (730) whether the respective power interval includes a train of power pulses 450. When the respective power interval includes a train of power pulses 450, the system determines (732) one or more of: the duration, the pulse pattern, the frequency, and the average power peak value of the train of power pulses 450. This is a respective subset of the power data characteristics 434 corresponding to the respective interval. When the respective power interval does not include a train of power pulses 450, the system determines (734) one or more of: the average current, the average voltage, the average active power, and the reactive power. This is a respective subset of the power data characteristics 434 corresponding to the respective interval.

In some embodiments, for each of the power intervals, the power cord server 108 compares the respective subset of the power data characteristics 434 corresponding to the respective interval with at least a respective power threshold 438. When a comparison for a first power interval satisfies an association criterion of a first operational state, the power cord server associates the first operational state with the first power interval, and determines the one or more numeric operational parameters 436 of the conducted medical procedure based on the respective subset of the power data characteristics 434 corresponding to the first power interval. Additionally, in some embodiments, the respective power threshold 438 associated with the first operational state is determined or adjusted based on a first deep learning technique.

Alternatively, in some embodiments, each of a subset of the power intervals (e.g., intervals corresponding to the trains of power pulse 450A and 450B in FIG. 4A) is directly analyzed using a deep learning model to classify the respective power interval as the operation mode 420, the idle mode 418, one of a plurality of operation states 422-432, and/or one of a plurality of medical procedures. In some embodiments, the deep learning model is trained in a supervised manner based on labelled training power profiles 120. In some embodiments, the deep learning model is trained in an unsupervised manner using the power profiles 120 collected from the medical devices 102. For example, as the deep learning model processes more and more power profiles 120, the deep learning model can classify power intervals more accurately and efficiently.

In some embodiments, the one or more numeric operational parameters 436 includes one or more first numeric operational parameters. The power cord server 108 receives (736) from a second cord device 106B, of a second power cable 104, a second power profile 120', which includes a plurality of second power data characteristics 434' measuring power delivered to a second medical device 102' while the second medical device 102' conducts the same medical procedure. The second power profile is used (738) to identify one or more second numeric operational parameters 436' of the same medical procedure. Further, in some embodiments, the power cord server 108 derives (740) a treatment power signature 440 for the same medical procedure based on at least the first and second numeric operational parameters 436 and 436' and generates (742) the message 130, including the treatment power signature 440, based on the first and second numeric operational parameters of the same medical procedure. Additionally, in some embodiments, a second electronic device receiving the message 130 is configured to adjust (744) the subsequent medical procedure performed by the second electronic device based on the treatment power signature 440 received in the message 130.

In some embodiments, the power profile 120 includes a first power profile, and the one or more numeric operational parameters 436 includes one or more first numeric operational parameters. The power cord server 108 receives (746) a plurality of third power profiles 120" from a plurality of third power cables 104C. Each of the plurality of third power profiles 120" includes a respective plurality of third power data characteristics 434" measuring power delivered to a respective third medical device 102C while the respective third medical device 102C conducts a respective third medical procedure. Each of the plurality of third power profiles 120" is used to identify (748) the respective third medical procedure, including one or more third numeric operational parameters 436" of the respective third medical procedure. The message 130 is generated (750) based on the one or more first numeric operational parameters 436 of the conducted medical procedure and the third numeric operational parameters 436" corresponding to the plurality of third power profiles 120". Additionally, in some embodiments, the first power profile 120 and the plurality of third power profiles 120" comply (752) with a geographical or temporal limitation, and the message 130 is generated based on the geographical or temporal limitation.

The power cord server 108 sends (754) a message 130 to a second electronic device for display on a user interface (e.g., the interfaces in FIGS. 5A-5C) of the second electronic device. The message 130 specifies the conducted medical procedure and the one or more numeric operational parameters 436. In some embodiments, the message 130 includes (756) an alert, a notification, a report, or an instruction concerning the conducted medical procedure. In some embodiments, the second electronic device includes the first medical device 102, and the second electronic device is configured to execute a power cord application 634A, including the user interface. The power cord server 108 enables (758) display of the message 130 on the user interface of the power cord application 634A of the first medical device 102. Alternatively, in some embodiments, the second electronic device includes the first medical device 102, and the first medical device is configured to execute a medical device application 630A including the user interface. The power cord server enables (760) display of the message 130 on the user interface of the medical device application 630A. The medical device application 630A is configured to implement the medical procedure. In some embodiments, the medical device application has a power cord plug-in program 632A, which is executed with the power cord server 108 to present the message 130.

Alternatively, in some embodiments, the second electronic device (e.g., a mobile phone) is distinct from the first medical device 102, and the second electronic device is configured to execute a power cord application 634B including the user interface. The power cord server 108 enables (762) display of the message on the user interface of the power cord application 634B of the second electronic device. The power cord application 634B is executed jointly with the power cord server 108. The second electronic device may have its own medical device application 630B.

Additionally and alternatively, in some embodiments, the second electronic device (e.g., a mobile phone) is distinct from the first medical device, and the second electronic device is configured to execute a medical device application 630A, including the user interface to implement one or more medical procedures. The power cord server 108 enables (764) display of the message 130 on the user interface in the medical device application 630A of the second electronic device. In some embodiments, the medical device application has a power cord plug-in program 632B, which is executed with the power cord server 108 to present the message 130.

It is noted that the power cord application is executed jointly with the power cord server 108, and distinct from a medical device application 630A, which is configured to perform the medical procedure. In some embodiments, the medical device application is online while the medical procedure is being performed, and executed jointly with a medical device server 114, which is distinct from the power cord server 108. In some embodiments, the medical device application 630A is offline while the medical procedure is being performed.

In some embodiments, the message is generated and sent (766) to the second electronic device according to a second reporting schedule. In some embodiments, the message is generated and sent (768) ad hoc to the second electronic device when the one or more numeric operational parameters of the conducted medical procedure satisfy second reporting criteria.

It should be understood that the particular order in which the operations in FIGS. 7A-7D have been described are merely exemplary and are not intended to indicate that the described order is the only order in which the operations could be performed. One of ordinary skill in the art would recognize various ways to manage power data as described herein. Additionally, it should be noted that details described above with respect to FIGS. 1-6C are also applicable in an analogous manner to the method 700 described above with respect to FIGS. 7A-7D. For brevity, these details are not repeated here.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another (e.g., according to a communication protocol). In this manner, computer-readable media generally may correspond to (1) tangible computer-readable storage media which is non-transitory or (2) a communication medium, such as a signal or carrier wave. Data storage media may be any available media that can be accessed by one or more computers or one or more processors to retrieve instructions, code and/or data structures for implementation of the embodiments described in the present application. A computer program product may include a computer-readable medium.

The terminology used in the description of the embodiments herein is for the purpose of describing particular embodiments only and is not intended to limit the scope of claims. As used in the description of the embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, elements, and/or components, but do not preclude the presence or addition of one or more other features, elements, components, and/or groups thereof.

It will also be understood that, although the terms first and second may be used herein to describe various elements, these elements should not be limited by these terms. These terms are only used to distinguish one element from another. For example, a first electrode could be termed a second electrode, and, similarly, a second electrode could be termed a first electrode, without departing from the scope of the embodiments. The first electrode and the second electrode are both electrodes, but they are not the same electrode.

The description of the present application has been presented for purposes of illustration and description, and is not intended to be exhaustive or limited to the invention in the form disclosed. Many modifications, variations, and alternative embodiments will be apparent to those of ordinary skill in the art having the benefit of the teachings presented in the foregoing descriptions and the associated drawings. The embodiments are described in order to best explain the principles of the invention, the practical application, and to enable others skilled in the art to understand the invention for various embodiments and to best utilize the underlying principles and various embodiments with various modifications as are suited to the particular use contemplated. Therefore, the scope of the claims is not to be limited to the specific examples of the embodiments disclosed. Modifications and other embodiments are intended to be included within the scope of the appended claims.

What is claimed is:

1. A method for collaboratively implementing medical procedures by distributed medical devices via smart power cords, comprising:
- communicatively coupling a server system hosting a centralized power data management system to a plurality of remote medical devices located at one or more medical facilities, including:
  - electrically coupling the plurality of remote medical devices to respective power sources using a plurality of power cables each including a cord device; and
  - for each of the power cables;
    - electrically coupling to, and powering, a respective remote medical device, the plurality of remote medical devices including a first medical device powered by a first power cable including a first cord device; and
    - while powering the respective remote medical device, communicatively coupling the server system to the respective remote medical device via one or more wide area networks (WANs);
- collecting, by the first cord device, a plurality of power data characteristics measuring power delivered to the first medical device powered by the first power cable while the first medical device conducts a medical procedure;
- generating a power profile by the first cord device based on the plurality of power data characteristics measuring the power delivered to the first medical device;
- communicating the power profile corresponding to the medical procedure conducted by the first medical device to the server system via the one or more WANs;
- based on the power profile, at the server system, determining one or more numeric operational parameters of the conducted medical procedure, and identifying the conducted medical procedure based on the one or more numeric operational parameters of the conducted medical procedure;
- generating, by the server system, a message specifying the conducted medical procedure and the one or more numeric operational parameters; and
- sending, from the server system to a second electronic device, an instruction for displaying the message on a user interface of the second electronic device, remotely guiding a distinct procedure to be implemented by a distinct medical device.

2. The method of claim 1, wherein the power profile corresponds to a plurality of operational states including a plurality of: a system idle state, a system initiation state, a treatment initiation state, one or more treatment states, a treatment idle state, and a power off state, and identifying the conducted medical procedure further comprises:
- identifying a subset of the plurality of operational states of the conducted medical procedure.

3. The method of claim 2, wherein the one or more treatment states include a first treatment state in which a train of power pulses are applied, and the plurality of power data characteristics include a duration, a frequency, a power pattern, and an average power peak value of the train of power pulses, the method further comprising:
- determining the one or more numeric operational parameters of the conducted medical procedure based on a subset of the power data characteristics corresponding to the first treatment state.

4. The method of claim 2, wherein each of the plurality of operational states is defined according to at least one power threshold associated with a respective subset of the power data characteristics, the method further comprising:

determining and adjusting the at least one power threshold associated with each of the plurality of operational states based on a deep learning technique.

5. The method of claim 1, wherein using the power profile to identify the conducted medical procedure further comprises:

dividing the power profile into a plurality of power intervals; and for each of the power intervals:

determining whether the respective power interval includes a train of power pulses;

in accordance with a determination that the respective power interval includes a train of power pulses, determining one or more of a duration, a pulse pattern, a frequency, and an average power peak value of the train of power pulses as a respective subset of the power data characteristics corresponding to the respective interval; and in accordance with a determination that the respective power interval does not include a train of power pulses, determining one or more of an average current, an average voltage, an average active power, and a reactive power as the respective subset of the power data characteristics corresponding to the respective interval.

6. The method of claim 5, wherein using the power profile to identify the conducted medical procedure further comprises:

for each of the power intervals, comparing the respective subset of the power data characteristics corresponding to the respective interval with at least a respective power threshold;

in accordance with a determination that a comparison for a first power interval satisfies an association criterion of a first operational state, associating the first operational state with the first power interval; and determining the one or more numeric operational parameters of the conducted medical procedure based on the respective subset of the power data characteristics corresponding to the first power interval.

7. The method of claim 1, the one or more numeric operational parameters including one or more first numeric operational parameters, the method further comprising:

receiving from a second cord device of a second power cable a second power profile including a plurality of second power data characteristics measuring power delivered to a second medical device while the second medical device conducts the same medical procedure; and using the second power profile to identify one or more second numeric operational parameters of the same medical procedure;

wherein the message is generated based on the first and second numeric operational parameters of the same medical procedure.

8. The method of claim 7, further comprising:

deriving a treatment power signature for the same medical procedure based on at least the first and second numeric operational parameters; and generating the message including the treatment power signature, wherein the second electronic device is configured to adjust a subsequent medical procedure performed by the second electronic device based on the treatment power signature received in the message.

9. The method of claim 1, the power profile including a first power profile, the one or more numeric operational parameters including one or more first numeric operational parameters, the method further comprising:

receiving a plurality of third power profiles from a plurality of third power cables, each of the plurality of third power profiles including a respective plurality of third power data characteristics measuring power delivered to a respective third medical device while the respective third medical device conducts a respective third medical procedure; and using each of the plurality of third power profiles to identify the respective third medical procedure, including one or more third numeric operational parameters of the respective third medical procedure;

wherein the message is generated based on the one or more first numeric operational parameters of the conducted medical procedure and the third numeric operational parameters corresponding to the plurality of third power profiles.

10. The method of claim 9, wherein the first power profile and the plurality of third power profiles comply with a geographical or temporal limitation, and the message is generated based on the geographical or temporal limitation.

11. A non-transitory computer-readable medium storing one or more programs configured for execution by one or more processors of a server system, the one or more programs comprising instructions for:

communicatively coupling a server system hosting a centralized power data management system to a plurality of remote medical devices located at one or more medical facilities, including:

electrically coupling the plurality of remote medical devices to respective power sources using a plurality of power cables each including a cord device; and for each of the power cables;

electrically coupling to, and powering, a respective remote medical device, the plurality of remote medical devices including a first medical device powered by a first power cable including a first cord device; and while powering the respective remote medical device, communicatively coupling the server system to the respective remote medical device via one or more wide area networks (WANs);

collecting, by the first cord device, a plurality of power data characteristics measuring power delivered to the first medical device powered by the first power cable while the first medical device conducts a medical procedure;

generating a power profile by the first cord device based on the plurality of power data characteristics measuring the power delivered to the first medical device;

communicating the power profile corresponding to the medical procedure conducted by the first medical device to the server system via the one or more WANs;

based on the power profile, at the server system, determining one or more numeric operational parameters of the conducted medical procedure, and identifying the conducted medical procedure based on the one or more numeric operational parameters of the conducted medical procedure;

generating, by the server system, a message specifying the conducted medical procedure and the one or more numeric operational parameters; and sending, from the server system to a second electronic device, an instruction for displaying the message on a user interface of the second electronic device, remotely guiding a distinct procedure to be implemented by a distinct medical device.

12. The non-transitory computer-readable medium of claim 11, wherein the second electronic device includes the first medical device, and the second electronic device is configured to execute a power cord application including the user interface, the one or more programs further comprising instructions for:

enabling display of the message on the user interface of the power cord application of the first medical device, wherein the power cord application is executed jointly with the server system, and distinct from a medical device application that is configured to perform the medical procedure.

13. The non-transitory computer-readable medium of claim 11, wherein the second electronic device includes the first medical device, and the first medical device is configured to execute a medical device application including the user interface, the one or more programs further comprising instructions for:

enabling display of the message on the user interface of the medical device application, wherein the medical device application is configured to implement the medical procedure.

14. The non-transitory computer-readable medium of claim 11, wherein the second electronic device is distinct from the first medical device, and the second electronic device is configured to execute a power cord application including the user interface, the one or more programs further comprising instructions for:

enabling display of the message on the user interface of the power cord application of the second electronic device, wherein the power cord application is executed jointly with the server system.

15. The non-transitory computer-readable medium of claim 11, wherein the second electronic device is distinct from the first medical device, and the second electronic device is configured to execute a medical device application including the user interface to perform one or more medical procedures, the one or more programs further comprising instructions for:

enabling display of the message on the user interface in the medical device application of the second electronic device.

16. An electronic system, comprising:

one or more processors; and memory storing one or more programs configured for execution by the one or more processors, the one or more programs comprising instructions for:

communicatively coupling a server system hosting a centralized power data management system to a plurality of remote medical devices located at one or more medical facilities, including:

electrically coupling the plurality of remote medical devices to respective power sources using a plurality of power cables each including a cord device; and for each of the power cables:

electrically coupling to, and powering, a respective remote medical device, the plurality of remote medical devices including a first medical device powered by a first power cable including a first cord device; and while powering the respective remote medical device, communicatively coupling the server system to the respective remote medical device via one or more wide area networks (WANs);

collecting, by the first cord device, a plurality of power data characteristics measuring power delivered to the first medical device powered by the first power cable while the first medical device conducts a medical procedure;

generating a power profile by the first cord device based on the plurality of power data characteristics measuring the power delivered to the first medical device;

communicating the power profile corresponding to the medical procedure conducted by the first medical device to the server system via the one or more WANs;

based on the power profile, at the server system, determining one or more numeric operational parameters of the conducted medical procedure, and identifying the conducted medical procedure based on the one or more numeric operational parameters of the conducted medical procedure;

generating, by the server system, a message specifying the conducted medical procedure and the one or more numeric operational parameters; and sending, from the server system to a second electronic device, an instruction for displaying the message on a user interface of the second electronic device, remotely guiding a distinct procedure to be implemented by a distinct medical device.

17. The electronic system of claim 16, wherein the power profile is streamed from the first cord device of the first power cable in real time while the first medical device conducts the medical procedure or received from the first cord device of the first power cable after the first medical device completes conduction of the medical procedure.

18. The electronic system of claim 16, wherein a batch of power profiles from the first cord device of the first power cable are received in a single transmission, the batch including the power profile together with one or more additional power profiles of one or more additional medical procedures, each of the additional procedures previously conducted at the first medical device, according to a first reporting schedule.

19. The electronic system of claim 16, wherein the message includes an alert, a notification, a report, or an instruction concerning the conducted medical procedure, and wherein the message is generated and sent to the second electronic device according to a second reporting schedule or ad hoc in accordance with a determination that the one or more numeric operational parameters of the conducted medical procedure satisfy reporting criteria.

20. The electronic system of claim 16, wherein the one or more wide area networks (WANs) includes a cellular network, and the plurality of power cables are communicatively coupled to the server system via the cellular network without accessing any local network device or local area network.

* * * * *